United States Patent
Moliner et al.

(10) Patent No.: US 8,012,993 B2
(45) Date of Patent: Sep. 6, 2011

(54) STABLE S-NITROSOTHIOLS, METHOD OF SYNTHESIS AND USE

(75) Inventors: José Repollés Moliner, Barcelona (ES); Francisco Pubill Coy, Cabrils (ES); Marisabel Mourelle Mancini, Barcelona (ES); Juan Carlos del Castillo Nieto, Barelona (ES); Lydia Cabeza Llorente, Barcelona (ES); Juan Martínez Bonín, Barcelona (ES); Ana Modolell Saladrigas, Barcelona (ES)

(73) Assignee: Lacer, S.A., Baarcelona (ES)

( * ) Notice: Subject to any disclaimer, the term of this patent is extended or adjusted under 35 U.S.C. 154(b) by 1163 days.

(21) Appl. No.: 11/680,815

(22) Filed: Mar. 1, 2007

(65) Prior Publication Data
US 2008/0161354 A1  Jul. 3, 2008

(30) Foreign Application Priority Data

Dec. 28, 2006 (EP) .................................. 06380340

(51) Int. Cl.
*A61K 31/445* (2006.01)
*C07D 211/00* (2006.01)

(52) U.S. Cl. ........ 514/318; 514/315; 514/327; 514/432; 546/193; 546/194; 546/216; 546/242; 546/246; 549/28; 549/416

(58) Field of Classification Search ............... 514/315, 514/318, 327, 432; 546/193, 194, 216, 242, 546/246; 549/28, 416
See application file for complete search history.

(56) References Cited

U.S. PATENT DOCUMENTS

| 6,800,612 B2 * | 10/2004 | Repolles Moliner et al. .. | 514/19 |
| 6,800,812 B1 * | 10/2004 | Franks, Jr. ................... | 174/136 |

FOREIGN PATENT DOCUMENTS

| EP | 0412699 | 2/1991 |
| EP | 1157987 | 11/2001 |
| WO | 9309806 | 5/1993 |
| WO | 9507691 | 3/1995 |
| WO | 9512394 | 5/1995 |
| WO | 03086282 | 10/2003 |

OTHER PUBLICATIONS

Fang et al. "preparation and compositions of nitrosothio . . . " Ca 139:350474 (2003).*
Flouret et al. "Design of novel . . . " CA145:315250 (2006).*
Radomski et al., "S-Nitroso-Glutathione Inhibits Platelet Activation in vitro and in vivo," Br. J. Pharmacol., vol. 107 (1992), pp. 745-749.
Smith et al., "In Vitro Vasorelaxant and In Vivo Cardiovascular Effects of S-Nitrosothiols: Comparison to and Cross Tolerance with Standard Nitrovasodilators," Meth Find Exp Clin Pharmacol, vol. 16, No. 5, (1994), pp. 323-335.
Golino et al., "Endothelium-Derived Relaxing Factor Modulates Platelet Aggregation in an In Vivo Model of Recurrent Platelet Activation," Circulation Research, vol. 71, No. 6, (Dec. 1992), pp. 1447-1456.

* cited by examiner

*Primary Examiner* — Celia Chang
(74) *Attorney, Agent, or Firm* — Tristan A. Fuierer; Moore & Van Allen PLLC

(57) ABSTRACT

The present invention relates to stable S-nitrosothiols derivatives of formula (I)

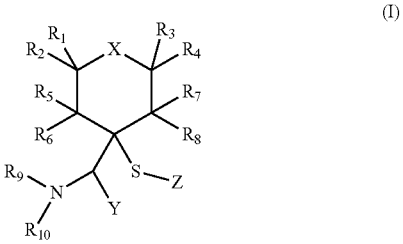

having vasodilating effect and which inhibit the aggregation of the platelets and which therefore are useful for the preparation of medicaments for treatment of NO related diseases. The invention also relates to a process for the synthesis of the compounds of formula (I).

17 Claims, No Drawings

STABLE S-NITROSOTHIOLS, METHOD OF SYNTHESIS AND USE

CROSS REFERENCE TO RELATED APPLICATIONS

This application claims priority to European Patent Application No. EP06380340.7, filed Dec. 28, 2006 and entitled "Stable S-Nitrosothiols, Method of Synthesis and Use" in the name of José Repollés Moliner et al., which is incorporated by reference herein.

FIELD OF THE INVENTION

The present invention relates to stable S-nitrosothiols derivatives useful for the preparation of medicaments for treatment of NO related diseases, to their synthesis, and intermediates thereof.

BACKGROUND OF THE INVENTION

It is well known that compounds capable of releasing nitrogen oxide (NO) into the organism exhibit in many cases some type of activity of the vascular system, for example vasodilating activity or inhibition of the aggregation of the platelets, which make them potentially useful for the treatment of different disorders related to dysfunctions of the circulatory system.

Further, it is described too that specific derivatives which contain an S-nitrosothiol group have, from a medical point of view, advantageous characteristics due to the fact that they are capable of releasing NO in the organism.

Radomski et al., *Br. J. Pharmacol.* (1992) 107, 745-749, describes that an S-nitrosoglutathione (GSNO) compound is capable of inhibiting the activity of the platelets.

Golino et al, *Circulation Research,* 71, No 6 (1992), describes that S-nitrosocysteine is capable of inhibiting the activity of the platelets, due to an anti-thrombosis effect.

Smith et al., *Met. Find. Exp. Clime. Pharmacy.* (1994), 16, 5, describes that the GSNO produces a strong relaxing effect of the arterioles.

WO95/12394 describes the use of S-nitroso adducts of peptides, among others the S-nitroso-N-acetylpenicillamine (SNAP), as protecting agents against vascular inflammation of traumatic origin.

WO95/07691 describes the use of different S-nitrosothiols, in particular the GSNO, in the treatment and prevention of the action of the platelets and the formation of thrombosis on damaged vascular surface.

WO93/09806 describes S-nitrosated proteins or amino acid residues, capable of releasing NO, which have a relaxing effect on the musculature and an inhibitory effect on platelet aggregation.

The S-nitrosothiol group is an unstable functional group and therefore the administration of active ingredients comprising the same possess many problems. The in vivo decomposition of the S-nitrosothiol functionality reduces the efficacy of some medicaments which show excellent in vitro activity. A further problem derived from the low stability of S-nitroso compounds is their short shelf stability.

EP-B1-1157987, in the name of the applicant, describes S-nitrosothiols derivatives of penicillamine or glutathione, which both have a potent vasodilating effect and a high inhibitory effect on the aggregation of the platelets of the formula

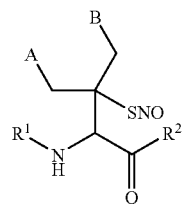

wherein A and B are phenyl groups or together form the residue —$CH_2$-Q-$CH_2$—constituting a ring of six units in which Q represents an atom of oxygen, of sulfur, or a group N—$R_3$, in which $R_3$ is hydrogen or an alkyl group $C_1$-$C_4$; $R_1$ is an acyl residue, which may be an aliphatic acyl group $C_1$-$C_5$ or a residue of glutamic acid bound via its non amino acid carboxyl; $R_2$ is a hydroxyl group or a glycine residue bound via a peptide bond. Although they show high efficacy, their usefulness is reduced due to the poor stability of the S-nitrosothiol functionality.

EP-B1-412699 describes S-nitrosothiols which correspond to following general formula:

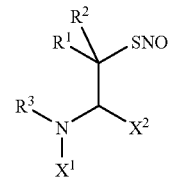

and its use as therapeutic agents against cardiovascular diseases, in particular as anti-hypertension (increased blood pressure) and as agents for the treatment of angina pectoris. According to EP-B1-412699 the S-nitrosothiol functional group may be stabilized by bulky $R_1$ and $R_2$ groups.

Thus, there is a need for providing stable S-nitrosothiol derivatives.

SUMMARY OF THE INVENTION

The inventors have know surprisingly found that the provision of compounds similar to those described in EP-B1-1157987 but having an ester group instead of an acid or a glycine amide, provides stable S-nitrosothiol derivatives.

Thus, a first aspect of the present invention relates to compounds of formula (I) (compounds of the invention) as described below.

A second aspect of the invention relates to the synthesis of said compounds of formula (I).

A further aspect is directed to a pharmaceutical composition comprising the compounds of formula (I) wherein Z is NO and a pharmaceutically acceptable carrier.

A further aspect is directed to a method of manufacturing a medicament comprising combining a compound of formula (I) wherein Z is NO and a pharmaceutically acceptable carrier.

A further aspect is directed to a method for the treatment and/or prophylaxis of a NO mediated condition comprising administering to a patient in need of such treatment a therapeutically effective amount of a compound of formula (I) wherein Z is NO.

DETAILED DESCRIPTION OF THE INVENTION

Compounds of Formula (I)

A first aspect of the present invention relates to compounds of formula (I)

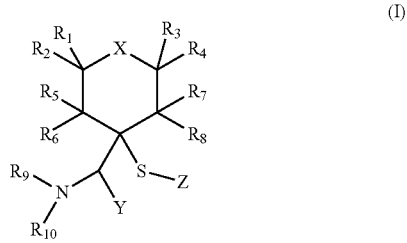

wherein

- $R_1$ and $R_3$ are each independently selected from the group consisting of hydrogen, alkyl, alkenyl, cycloalkyl and alkynyl; or $R_1$ and $R_3$ together form a 5 or 6 membered ring which includes X;
- $R_2$, $R_4$, $R_5$, $R_6$, $R_7$ and $R_8$ are each independently selected from the group consisting of hydrogen, alkyl, alkenyl, cycloalkyl and alkynyl;
- $R_9$ is selected from the group consisting of hydrogen, alkyl, alkenyl, cycloalkyl, alkynyl, aryl and aralkyl;
- $R_{10}$ is selected from the group consisting of hydrogen, alkyl, cycloalkyl, alkenyl, alkynyl, heterocyclyl, —C(=O)$R_{11}$ and —S(=O)$_2R_{11}$, wherein $R_{11}$ is selected from the group consisting of hydrogen, alkyl, alkenyl, cycloalkyl, alkynyl, aryl, aralkyl and heterocyclyl;
- Z is selected from the group consisting of hydrogen, NO, unsubstituted alkyl, alkenyl, $C_7$-$C_{20}$ aralkyl, —Si(R')$_3$ and C(=O)R', wherein R' is selected from the group consisting of alkyl, alkenyl, alkynyl, aryl and aralkyl;
- Y is an alkoxycarbonyl of formula —C(=O)O$R_{12}$, wherein $R_{12}$ is selected from the group consisting of alkyl, alkenyl, cycloalkyl, alkynyl, aryl, aralkyl, and heterocyclyl; and
- X is selected from the group consisting of oxygen atom, sulphur atom, and —N$R_{13}$; wherein $R_{13}$ is selected from the group consisting of hydrogen, alkyl, alkenyl, cycloalkyl, alkynyl, aryl, aralkyl and heterocyclyl;

or its salts or solvates thereof.

The invention also provides salts of compounds of the invention. For instance, pharmaceutically acceptable salts of compounds provided herein may be acid addition salts, base addition salts or metallic salts, and they can be synthesized from the parent compound which contains a basic or an acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

The term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

It will be readily apparent to those skilled in the art that the scope of the present invention also encompasses salts which are not pharmaceutically acceptable as possible means for obtaining pharmaceutically acceptable salts.

The term "solvate" according to this invention is to be understood as meaning any form of the active compound according to the invention which has another molecule (most likely a polar solvent) attached to it via non-covalent bonding. Examples of solvates include hydrates and alcoholates, preferably $C_1$-$C_6$ alcoholates, e.g. methanolate.

It will be immediately apparent to the skilled person that the present invention encompasses all possible stereoisomers of the compounds described herein. An stereoisomer is understood by the skilled person as compounds made up of the same atoms bonded by the same sequence of bonds but having different three-dimensional structures which are not interchangeable.

According to a preferred embodiment, Z is NO.

According to a preferred embodiment, each of $R_5$, $R_6$, $R_7$ and $R_8$ is hydrogen.

According to a preferred embodiment, the compounds of the invention are compounds of formula (II):

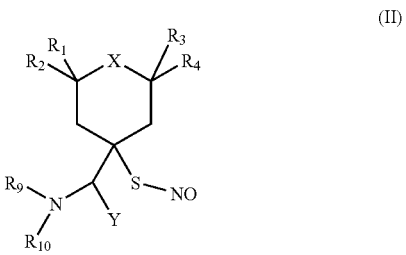

wherein

- $R_1$ and $R_3$ are each independently selected from the group consisting of hydrogen and $C_1$-$C_4$ alkyl; or $R_1$ and $R_3$ together form a 5 or 6 member ring which includes X;
- $R_2$ and $R_4$ are each independently selected from the group consisting of hydrogen and $C_1$-$C_4$ alkyl;
- $R_9$ is selected from the group consisting of hydrogen, $C_1$-$C_6$ alkyl and $C_7$-$C_{15}$ aralkyl;
- $R_{10}$ is selected from the group consisting of hydrogen, $C_1$-$C_6$ alkyl, $C_3$-$C_8$ cycloalkyl, —C(=O)$R_{11}$ and —S(=O)$_2R_{11}$, wherein $R_{11}$ is selected from the group consisting of hydrogen, $C_1$-$C_6$ alkyl, $C_2$-$C_6$ alkenyl, $C_3$-$C_8$ cycloalkyl, $C_2$-$C_6$ alkynyl, $C_6$-$C_{10}$ aryl, $C_7$-$C_{10}$ aralkyl and heterocyclyl;
- Y is an alkoxycarbonyl of formula —C(=O)O$R_{12}$, wherein $R_{12}$ is selected from the group consisting of $C_1$-$C_6$ alkyl, $C_2$-$C_6$ alkenyl, $C_3$-$C_8$ cycloalkyl, $C_2$-$C_6$ alkynyl, $C_6$-$C_{10}$ aryl, $C_7$-$C_{10}$ aralkyl and heterocyclyl; and X is selected from the group consisting of oxygen atom, sulphur atom, $NR_{13}$,
wherein $R_{13}$ is selected from the group consisting of hydrogen, $C_1$-$C_6$ alkyl group, $C_2$-$C_6$ alkenyl, $C_3$-$C_8$ cycloalkyl, $C_2$-$C_6$ alkynyl, $C_6$-$C_{10}$ aryl, $C_7$-$C_{10}$ aralkyl and heterocyclyl;

or its salts or solvates thereof.

A further preferred embodiment are compounds of formula (IIa)

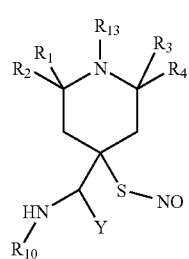

(IIa)

wherein
$R_1$ and $R_3$ are each independently selected from the group consisting of hydrogen and $C_1$-$C_4$ alkyl; or $R_1$ and $R_3$ together form a 5 or 6 member ring which includes X;
$R_2$ and $R_4$ are each independently selected from the group consisting of hydrogen and $C_1$-$C_4$ alkyl;
$R_{10}$ is selected from the group consisting of —C(=O)$R_{11}$ and —S(=O)$_2R_{11}$, wherein
$R_{11}$ is selected from the group consisting of H, $C_1$-$C_6$ alkyl, $C_6$-$C_{10}$ aryl, $C_7$-$C_{10}$ aralkyl and heterocyclyl; and
Y is an alkoxycarbonyl of formula C(=O)O$R_{12}$, wherein $R_{12}$ is a $C_1$-$C_6$ alkyl;

or its salts or solvates thereof.

According to a preferred embodiment, each of $R_1$, $R_2$, $R_3$ and $R_4$ is hydrogen.

According to a preferred embodiment, X is —$NR_{13}$, wherein $R_{13}$ is defined as above.

According to a preferred embodiment, $R_9$ is selected from the group consisting of hydrogen and $C_1$-$C_6$ alkyl.

According to a preferred embodiment, $R_{12}$ is a $C_1$-$C_6$ alkyl group.

According to a preferred embodiment, one of $R_9$ or $R_{10}$ is hydrogen.

According to a preferred embodiment, the compounds of the invention are selected from the group consisting of:

Ethyl(R,S)-acetylamino-(1-methyl-4-S-nitrosomercapto-piperidin-4-yl)-acetate;
(R,S)-4-(Acetylamino-ethoxycarbonyl-methyl)-1-methyl-4-S-nitrosomercapto-piperidinium chloride;
Ethyl(R,S)-heptanoylamino-(1-methyl-4-S-nitrosomercapto-piperidin-4-yl)-acetate;
(R,S)-4-(Heptanoylamino-ethoxycarbonyl-methyl)-1-methyl-4-S-nitrosomercapto-piperidinium chloride;
Ethyl(R,S)-benzoylamino-(1-methyl-4-S-nitrosomercapto-piperidin-4-yl)-acetate;
(R,S)-4-(Benzoylamino-ethoxycarbonyl-methyl)-1-methyl-4-S-nitrosomercapto-piperidinium chloride;
Ethyl(R,S)-(4-chloro-benzoylamino)-(1-methyl-4-S-nitrosomercapto-piperidin-4-yl)-acetate;
(R,S)-4-[(4-Chloro-benzoylamino)-ethoxycarbonyl-methyl)]-1-methyl-4-S-nitrosomercapto-piperidinium chloride;
Ethyl(R,S)-(2-chloro-benzoylamino)-(1-methyl-4-S-nitrosomercapto-piperidin-4-yl)-acetate;
(R,S)-4-[(2-Chloro-benzoylamino)-ethoxycarbonyl-methyl)]-1-methyl-4-S-nitrosomercapto-piperidinium chloride;
Ethyl(R,S)-(1-methyl-4-S-nitrosomercapto-piperidin-4-yl)-[(pyridin-3-carbonyl)-amino]-acetate;
(R,S)-4-{Ethoxycarbonyl-[(pyridin-3-carbonyl)-amino]-methyl}-1-methyl-4-S-nitrosomercapto-piperidinium chloride;
Ethyl(R,S)-benzenesulfonylamino-(1-methyl-4-S-nitrosomercapto-piperidin-4-yl)-acetate;
(R,S)-4-(Benzenesulfonylamino-ethoxycarbonyl-methyl)-1-methyl-4-S-nitrosomercapto-piperidinium chloride;
Ethyl(R,S)-(1-methyl-4-S-nitrosomercapto-piperidin-4-yl)-(4-nitro-benzene sulfonylamino)-acetate;
Ethyl(R,S)-(4-methyl-benzenesulfonylamino)-(1-methyl-4-S-nitrosomercapto-piperidin-4-yl)-acetate;
Ethyl(R,S)-(2-chloro-benzenesulfonylamino)-(1-methyl-4-S-nitrosomercapto-piperidin-4-yl)-acetate;
Ethyl(R,S)-(3-chloro-benzenesulfonylamino)-(1-methyl-4-S-nitrosomercapto-piperidin-4-yl)-acetate;
Ethyl(R,S)-(4-chloro-benzenesulfonylamino)-(1-methyl-4-S-nitrosomercapto-piperidin-4-yl)-acetate;
(R,S)-4-(4-Chloro-benzenesulfonylamino-ethoxycarbonyl-methyl)-1-methyl-4-S-nitrosomercapto-piperidinium chloride;
(R,S)-4-(2-Fluoro-benzenesulfonylamino-ethoxycarbonyl-methyl)-1-methyl-4-S-nitrosomercapto-piperidinium chloride;
Ethyl(R,S)-(4-fluoro-benzenesulfonylamino)-(1-methyl-4-S-nitrosomercapto-piperidin-4-yl)-acetate;
(R,S)-4-(4-Fluoro-benzenesulfonylamino-ethoxycarbonyl-methyl)-1-methyl-4-S-nitrosomercapto-piperidinium chloride;
Ethyl(R,S)-(2,4-difluoro-benzenesulfonylamino)-(1-methyl-4-S-nitroso mercapto-piperidin-4-yl)-acetate;
(R,S)-4-(2,4-Difluoro-benzenesulfonylamino-ethoxycarbonyl-methyl)-1-methyl-4-S-nitrosomercapto-piperidinium chloride;
Ethyl(R,S)-formylamino-(1-methyl-4-S-nitrosomercapto-piperidin-4-yl)-acetate;
(R,S)-4-(Ethoxycarbonyl-formylamino-methyl)-1-methyl-4-S-nitrosomercapto-piperidinium chloride;
Ethyl(R,S)-(1-methyl-4-S-nitrosomercapto-piperidin-4-yl)-(2,2,2-trifluoro-acetyl amino)-acetate;
Benzyl(R,S)-acetylamino-(1-methyl-4-S-nitrosomercapto-piperidin-4-yl)-acetate;
Ethyl(R,S)-(acetyl-ethyl-amino)-(1-methyl-4-S-nitrosomercapto-piperidin-4-yl)-acetate;
Ethyl(R,S)-acetylamino-(1-ethyl-4-S-nitrosomercapto-piperidin-4-yl)-acetate;
(R,S)-4-(Acetylamino-ethyloxycarbonyl-methyl)-1-ethyl-4-S-nitrosomercapto-piperidinium chloride;
Ethyl(R,S)-(1-ethyl-4-S-nitrosomercapto-piperidin-4-yl)-[(pyridin-3-carbonyl)-amino]-acetate;
(R,S)-1-Ethyl-4-{ethoxycarbonyl-[(pyridin-3-carbonyl)-amino]-methyl}-4-S-nitrosomercapto-piperidinium chloride;
Ethyl(R,S)-acetylamino-(1-benzyl-4-S-nitrosomercapto-piperidin-4-yl)-acetate;
(R,S)-4-(Acetylamino-ethyloxycarbonyl-methyl)-1-benzyl-4-S-nitrosomercapto-piperidinium chloride;
Ethyl(R,S)-(1-benzyl-4-S-nitrosomercapto-piperidin-4-yl)-[(pyridin-3-carbonyl)-amino]-acetate;

(R,S)-1-Benzyl-4-{ethoxycarbonyl-[(pyridin-3-carbonyl)-amino]-methyl}-4-S-nitrosomercapto-piperidinium chloride;
Ethyl(R,S)-(1-ethyl-4-S-nitrosomercapto-piperidin-4-yl)-formylamino-acetate;
(R,S)-1-Ethyl-4-(ethyloxycarbonyl-formylamino-methyl)-4-S-nitrosomercapto-piperidinium chloride;
Ethyl(R,S)-(1-benzyl-4-S-nitrosomercapto-piperidin-4-yl)-formylamino-acetate;
(R,S)-1-Benzyl-4-(ethyloxycarbonyl-formylamino-methyl)-4-S-nitrosomercapto-piperidinium chloride;
Methyl(R,S)-acetylamino-(1-methyl-4-S-nitrosomercapto-piperidin-4-yl)-acetate;
(R,S)-4-(Acetylamino-methyloxycarbonyl-methyl)-1-methyl-4-S-nitrosomercapto-piperidinium chloride;
Methyl(R,S)-(1-methyl-4-S-nitrosomercapto-piperidin-4-yl)-[(pyridin-3-carbonyl)-amino]-acetate;
Methyl(R,S)-benzenesulfonylamino-(1-methyl-4-S-nitrosomercapto-piperidin-4-yl)-acetate;
(R,S)-4-(Benzenesulfonylamino-methoxycarbonyl-methyl)-1-methyl-4-S-nitrosomercapto-piperidinium chloride;
Methyl(R,S)-formylamino-(1-methyl-4-S-nitrosomercapto-piperidin-4-yl)-acetate;
Ethyl(R,S)-acetylamino-(4-nitrosomercapto-tetrahydro-thiopyran-4-yl)-acetate; and
Ethyl(R,S)-benzenesulfonylamino-(4-nitrosomercapto-tetrahydro-thiopyran-4-yl)-acetate;
or solvates thereof.

According to an embodiment of the invention, the compounds of formula (I) are compounds of formula (III)

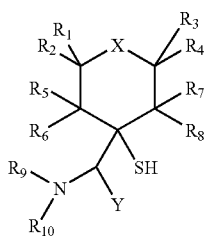

(III)

wherein
R$_1$ and R$_3$ are each independently selected from the group consisting of hydrogen, alkyl, alkenyl, cycloalkyl and alkynyl; or R$_1$ and R$_3$ together form a 5 or 6 membered ring which includes X;
R$_2$, R$_4$, R$_5$, R$_6$, R$_7$ and R$_8$ are each independently selected from the group consisting of hydrogen, alkyl, alkenyl, cycloalkyl and alkynyl;
R$_9$ is selected from the group consisting of hydrogen, alkyl, alkenyl, cycloalkyl, alkynyl, aryl and aralkyl;
R$_{10}$ is selected from the group consisting of hydrogen, alkyl, cycloalkyl, alkenyl, alkynyl, heterocyclyl, —C(=O)R$_{11}$ and —S(=O)$_2$R$_{11}$, wherein R$_{11}$ is selected from the group consisting of hydrogen, alkyl, alkenyl, cycloalkyl, alkynyl, aryl, aralkyl and heterocyclyl;
Y is an alkoxycarbonyl of formula —C(=O)OR$_{12}$, wherein R$_{12}$ is selected from the group consisting of alkyl, alkenyl, cycloalkyl, alkynyl, aryl, aralkyl, and heterocyclyl; and
X is selected from the group consisting of oxygen atom, sulphur atom, and —NR$_{13}$; wherein R$_{13}$ is selected from the group consisting of hydrogen, alkyl, alkenyl, cycloalkyl, alkynyl, aryl, aralkyl and heterocyclyl;
or its salts or solvates thereof.

The compounds of formula (III) are compounds of formula (I) wherein Z is a hydrogen atom.

According to an embodiment of the invention, the compounds of formula (I) are compounds of formula (IV)

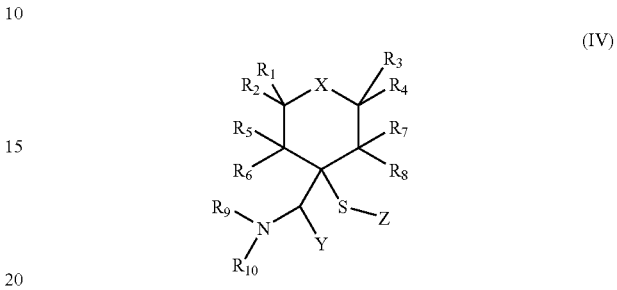

(IV)

wherein
R$_1$ and R$_3$ are each independently selected from the group consisting of hydrogen, alkyl, alkenyl, cycloalkyl and alkynyl; or R$_1$ and R$_3$ together form a 5 or 6 membered ring which includes X;
R$_2$, R$_4$, R$_5$, R$_6$, R$_7$ and R$_8$ are each independently selected from the group consisting of hydrogen, alkyl, alkenyl, cycloalkyl and alkynyl;
R$_9$ is selected from the group consisting of hydrogen, alkyl, alkenyl, cycloalkyl, alkynyl, aryl and aralkyl;
R$_{10}$ is selected from the group consisting of hydrogen, alkyl, cycloalkyl, alkenyl, alkynyl, heterocyclyl, —C(=O)R$_{11}$ and —S(=O)$_2$R$_{11}$, wherein R$_{11}$ is selected from the group consisting of hydrogen, alkyl, alkenyl, cycloalkyl, alkynyl, aryl, aralkyl and heterocyclyl;
Z is selected from the group consisting of unsubstituted alkyl, alkenyl, C$_7$-C$_{20}$ aralkyl, —Si(R')$_3$ and C(=O)R', wherein R' is selected from the group consisting of alkyl, alkenyl, alkynyl, aryl and aralkyl;
Y is an alkoxycarbonyl of formula —C(=O)OR$_{12}$, wherein R$_{12}$ is selected from the group consisting of alkyl, alkenyl, cycloalkyl, alkynyl, aryl, aralkyl, and heterocyclyl; and
X is selected from the group consisting of oxygen atom, sulphur atom, and —NR$_{13}$; wherein R$_{13}$ is selected from the group consisting of hydrogen, alkyl, alkenyl, cycloalkyl, alkynyl, aryl, aralkyl and heterocyclyl;
or its salts or solvates thereof.

The compounds of formula (IV) are compounds of formula (I), wherein Z is not NO.

Synthesis of the Compounds of Formula (I) and Intermediates of the Same

A second aspect of the invention is directed to a method for the synthesis of a compound of the invention comprising the addition of a compound of formula HS-Z, wherein Z is selected from the group consisting of hydrogen, unsubstituted alkyl, alkenyl, C$_7$-C$_{20}$ aralkyl, —Si(R')$_3$ and —C(=O) R', wherein R' is selected from the group consisting of alkyl, alkenyl, alkynyl, aryl and aralkyl, in the presence of a base, to a compound of formula (V)

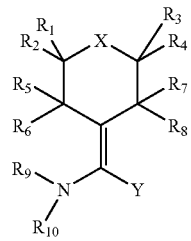

(V)

wherein
- $R_1$ and $R_3$ are each independently selected from the group consisting of hydrogen, alkyl, alkenyl, cycloalkyl and alkynyl; or $R_1$ and $R_3$ together form a 5 or 6 membered ring which includes X;
- $R_2$, $R_4$, $R_5$, $R_6$, $R_7$ and $R_8$ are each independently selected from the group consisting of hydrogen, alkyl, alkenyl, cycloalkyl and alkynyl;
- $R_9$ is selected from the group consisting of hydrogen, alkyl, alkenyl, cycloalkyl, alkynyl, aryl and aralkyl;
- $R_{10}$ is selected from the group consisting of hydrogen, alkyl, cycloalkyl, alkenyl, alkynyl, heterocyclyl, —C(=O)$R_{11}$ and —S(=O)$_2R_{11}$, wherein $R_{11}$ is selected from the group consisting of hydrogen, alkyl, alkenyl, cycloalkyl, alkynyl, aryl, aralkyl and heterocyclyl;
- Y is an alkoxycarbonyl of formula —C(=O)O$R_{12}$, wherein $R_{12}$ is selected from the group consisting of alkyl, alkenyl, cycloalkyl, alkynyl, aryl, aralkyl, and heterocyclyl; and
- X is selected from the group consisting of oxygen atom, sulphur atom, and —N$R_{13}$; wherein $R_{13}$ is selected from the group consisting of hydrogen, alkyl, alkenyl, cycloalkyl, alkynyl, aryl, aralkyl and heterocyclyl;

or its salts or solvates thereof;
and, if required, when Z is hydrogen in the resulting compound of formula (I), nitrosating the thiol functionality.

Nitrosation is achieved with reagents known to those skilled in the art and which may be found in text books such as "Advanced Organic Chemistry, Reactions, Mechanism, and Structure" 5$^{th}$ Edition, Wiley-Interscience (see pages 699, 779-780, 818 and references cited therein).

According to preferred embodiment, nitrosation comprises contacting said compound of formula (I) wherein Z is hydrogen (that is, a compound of formula (III)) with a reagent selected from the group consisting of nitrous acid, alkylnitrites, NO gas, NOCl, NOBr, $N_2O_3$, $N_2O_4$ and BrCH$_2$NO$_2$.

For example, nitrosation agents may be obtained by placing sodium nitrite in aqueous or hydroalcoholic acid media, i.e. hydrochloric media, or by placing an alkylnitrite (i.e. tert-butyl or amyl nitrite) in neutral media, such as any suitable organic solvent, i.e. alcohols (ethanol, methanol, . . . ), acetone, dichloromethane or tetrahydrofurane.

In U.S. Pat. No. 6,225,311 (Page 109) and WO 2000044709 A2 (page 293) the following compounds have been described wherein the Z group is 2-hydroxylethyl (substituted alkyl):

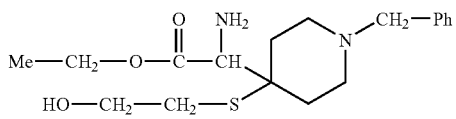

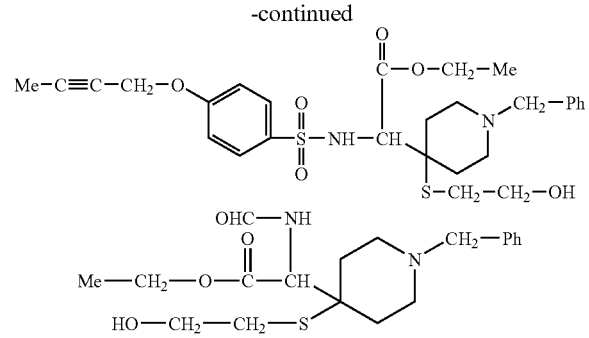

Z is usually selected so as to be easily cleaved at this stage of the synthesis. For example, thioethers, such as methyl thioether, tert-butyl thioether, benzyl thioether, p-methoxybenzyl thioether, 3,4-dimethoxybenzyl thioether, trityl thioether; allyl thioether; silyl derivatives of formula —Si(R')$_3$ such as trimethylsilyl (also represented as "TMS"), triethylsilyl, tert-butyldimethylsilyl (also represented as "TBDMSO"), tert-butyldiphenylsilyl, tri-isopropylsilyl, diethylisopropylsilyl, thexyldimethylsilyl ether, triphenylsilyl, di-tert-butylmethylsilyl; or thioesters such as acetate thioester, benzoate thioester; pivalate thioester; methoxyacetate thioester; chloroacetate thioester; levulinate thioester. Further conditions under which said groups may be removed, can be found in T. W. Greene and P. G. M. Wuts en "Protective Groups in Organic Synthesis", 3a Edicción, Wiley-Interscience, pages 454-493.

According to a preferred embodiment, the method involves the addition of a compound of formula HS-Z, wherein Z is a $C_7$-$C_{20}$ aralkyl group (e.g. p-methoxybencyl) which may be removed under standard conditions (see T. W. Greene et al.), such as acidic conditions (e.g. trifluoroactic acid) or hydrogenolysis.

According to an embodiment of the invention, the method comprises the following steps:
a) the addition of a compound of formula HS-Z, wherein Z is selected from the group consisting of unsubstituted alkyl, alkenyl, $C_7$-$C_{20}$ aralkyl, —Si(R')$_3$ and —C(=O)R', wherein R' is selected from the group consisting of alkyl, alkenyl, alkynyl, aryl and aralkyl, in the presence of a base, to a compound of formula (V)

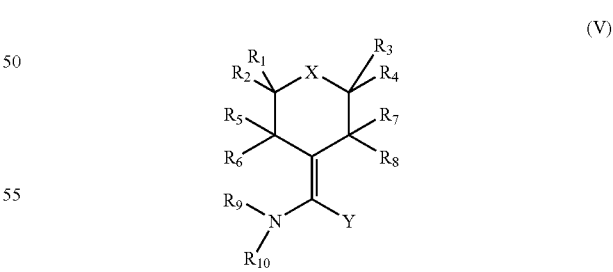

(V)

wherein
$R_1$, $R_2$, $R_3$, $R_4$, $R_5$, $R_6$, $R_7$, $R_8$, $R_9$, $R_{10}$, Y and X are as previously defined; to obtain the compound of formula (IV);
b) the removal of the Z group from the compound obtained in step a) to obtain a compound of formula (III); and
c) the nitrosation of the thiol functionality of the compound obtained in step b).

Conditions for performing step a) can be found in Nelson C. F. Yim et al., *J. Org. Chem.*, 1988, 53, 4605-7 and C. Freeman Stanfield et al., *Synthetic Communications*, 1988, 18(5), 531-43.

According to an embodiment of the invention, the method for the synthesis of the compounds of formula (I) comprises the following steps:

a) the addition of $SH_2$ to a compound of formula (V)

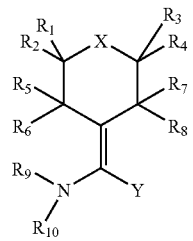

(V)

wherein $R_1$, $R_2$, $R_3$, $R_4$, $R_5$, $R_6$, $R_7$, $R_8$, $R_9$, $R_{10}$, Y and X are as previously defined, to obtain the compound of formula (III); and b) the nitrosation of the thiol functionality of the compound obtained in step a).

Thus, with this method it is possible to provide the compounds of formula (III) in a single step from the compounds of formula (V).

The compounds of formula (V) are readily available by reaction of ketones of formula (VI)

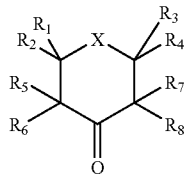

(VI)

wherein $R_1$, $R_2$, $R_3$, $R_4$, $R_5$, $R_6$, $R_7$, $R_9$ and X are as defined in formula (I); with alkylisocyanoacetates of formula (VII)

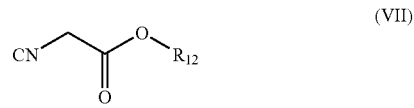

(VII)

wherein $R_{12}$ is as defined in formula (I).

The conditions for this reactions may be found in DE 2801849 and Nunami Kenichi et al., *J. Chem. Soc. Perkin Trans.* 1, 1979, 9, 2224-9. The resulting compounds of this process are compounds of formula (V) wherein $R_9$ is hydrogen and $R_{10}$ is a formyl group. Thus, if necessary, the appropriate functionality must be introduced in $R_9$ and $R_{10}$. This may be done by methods known to the skilled person at any stage of the synthesis of the compounds of the invention. For example, prior to the formation of the compounds of formula (I) or after the formation of the compounds of formula (I). Thus, once a compound of formula (I), such as a compound of formula (II) or a compound of formula (IV), is obtained, it is possible to undergo different transformations of $R_9$ and $R_{10}$ in order to obtain the desired functionality. The election of the precise stage at which to introduce or modify said $R_9$ and $R_{10}$ groups will depend on the compatibility of the different functional groups in the molecule. Said incompatibilities are a matter of common general knowledge or routine experimentation for the skilled person.

For example, it is possible to prepare a compound of formula (V) wherein $R_9$ is hydrogen and $R_{10}$ is a formyl group from a compound of formula (VI) and a compound of formula (VII) as described above, and then remove the formyl group. This sequence provides a compound of formula (V) wherein $R_9$ and $R_{10}$ are hydrogen. In further steps $R_9$ and $R_{10}$ groups may be introduced followed by removal of the Z group to obtain a compound of formula (III) and then nitrosation. Alternatively, $R_9$ and $R_{10}$ may be introduced prior to the formation of the compound of formula (IV), i.e. after hydrolysis of the formyl group. The above mentioned alternatives are shown bellow in scheme I.

Scheme I

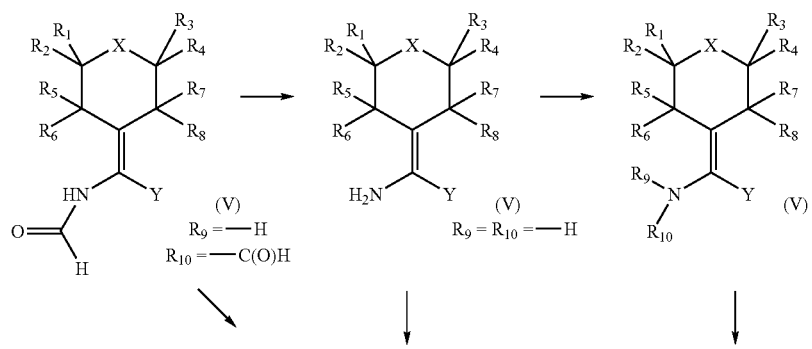

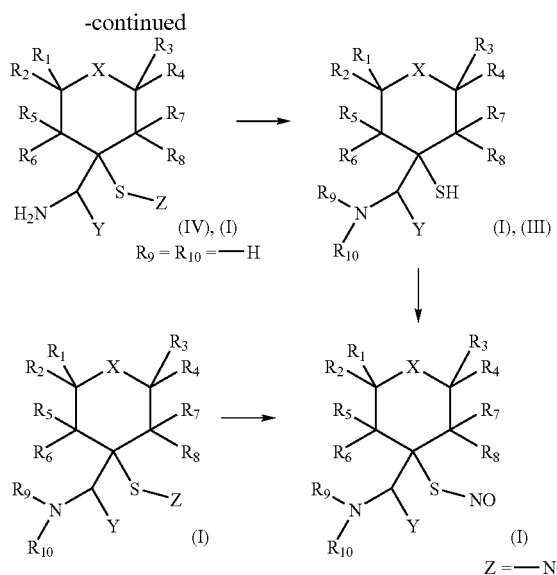

Another alternative is to prepare a compound of formula (V) wherein $R_9$ is hydrogen and $R_{10}$ is a formyl group form a compound of formula (VI) and a compound of formula (VII), transform said compound of formula (V) into a compound of formula (IV) (wherein $R_9$ is hydrogen and $R_{10}$ is formyl) and then remove the Z group to form a compound of formula (III) wherein $R_9$ is hydrogen and $R_{10}$ is formyl. Said compound of formula (III) wherein $R_9$ is hydrogen and $R_{10}$ is formyl may be used to prepare a compound of formula (I) wherein $R_9$ is hydrogen and $R_{10}$ is formyl. Alternatively, introduction of the $R_9$ and $R_{10}$ groups in said compound of formula (III), followed by nitrosation may also yield a compound of formula (I). The above mentioned alternatives are shown bellow in scheme II.

Scheme II

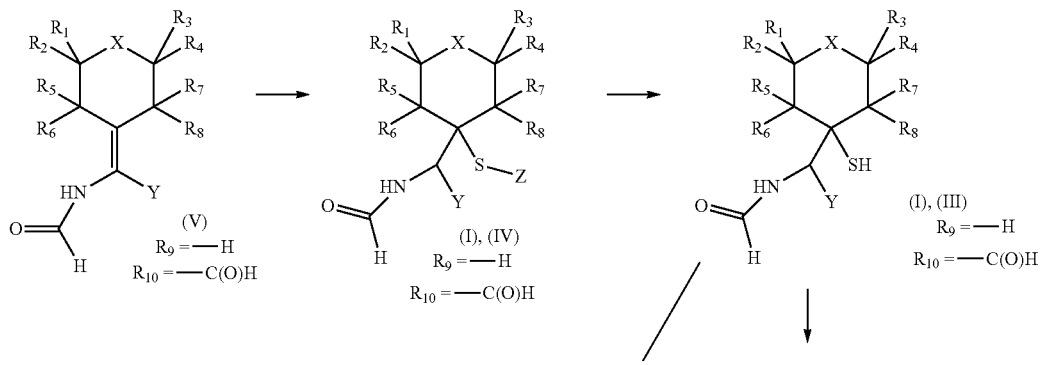

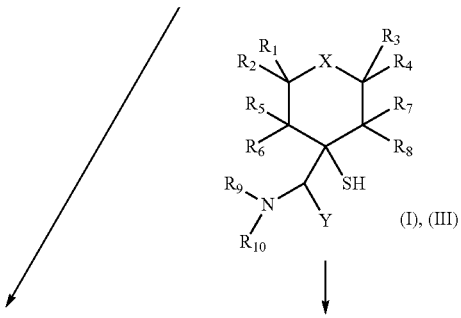

-continued

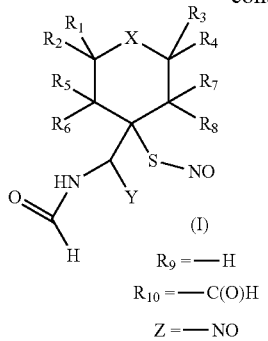

$R_9 = —H$
$R_{10} = —C(O)H$
$Z = —NO$

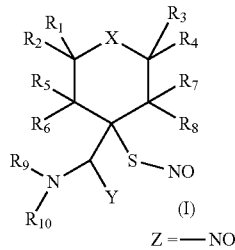

$Z = —NO$

In a further embodiment it is also possible to introduce $R_9$ and $R_{10}$ in non-consecutive steps at different points in the synthesis. Other possible combinations will be readily apparent to the skilled person.

Methods of Treatment and Pharmaceutical Compositions

A further aspect of the invention is a method for the treatment and/or prophylaxis of a NO mediated condition comprising administering to a patient in need of such treatment a therapeutically effective amount of a compound of formula (I) wherein Z is NO.

The term "treatment and/or prophylaxis" in the context of this specification means administration of a compound or formulation according to the invention to preserve health in a patient suffering or in risk of suffering a NO mediated condition. Said terms also include administration of a compound or formulation according to the invention to prevent, ameliorate or eliminate one or more symptoms associated with a NO mediated condition.

The compounds of the invention have shown increased stability with respect to those described in EP-B1-1157987 and comparable vasodilating activity and inhibitory effect on the aggregation of the platelets.

According to a preferred embodiment said NO mediated condition is platelet dysfunction, endocrine, metabolic, cardiovascular, inflammatory, genitourinary, digestive, dermatological, neuronal, central nervous system related, neurodegenerative diseases, mental disorders, cognitive disorders, respiratory or infectious conditions.

According to a further preferred embodiment, said NO mediated condition is hypertension, thrombosis, thromboembolic processes, vascular or trauma inflammation, complications associated to diabetes, ischemia-reperfusion, carotid endarterectomy and coronary bypass, graft rejections, in percutaneous coronary interventions, as vascular tone modulator, infant respiratory distress syndrome, asthma, pulmonary hypertension, bronchopulmonary dysplasia, cystic fibrosis, infectious diseases caused by bacteria, viruses and protozoa, Leishmaniasis, Trypanosomiasis, inhibition of AIDS virus replication, gastrointestinal tract motor diseases, inflammatory bowel disease, achalasia, diseases of the gall-bladder and the sphincter of Oddi, in cholangiopancreotography, liver failure, hepatic fibrosis, hepatic cirrhosis, portal hypertension, genitourinary tract diseases and erectile dysfunction, preeclampsia, endometrial hyperplasia, uterine smooth muscle proliferation, myometrium tumors, skin ulcers, ulcers related to diabetis, Alzheimer's disease, pain and fibromyalgias.

According to a further preferred embodiment said NO mediated condition is an ophthalmological disease caused or related to ocular hypertension, in particular glaucoma.

According to a further aspect, the present invention is directed to a pharmaceutical composition comprising a compound of formula (I) wherein Z is NO and a pharmaceutically acceptable carrier.

A further aspect of the invention is a method of manufacturing a medicament comprising combining a compound of formula (I) wherein Z is NO and a pharmaceutically acceptable carrier.

The term "carrier" refers to a diluent, adjuvant, excipient, or vehicle with which the active ingredient is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions, also buffers, isotonic agents or agents capable increasing solubility. Suitable pharmaceutical carriers are described in "Remington's Pharmaceutical Sciences" by E. W. Martin or "Tratado de Farmacia Galénica", C. Faulí i Trillo, Luzán 5, S. A. de Ediciones, 1993.

The pharmaceutical composition of the invention may be administered in the form of different preparations. Non limiting examples are preparations for oral administration, e.g. tablets, capsules, syrups or suspensions; ophthalmological administration, e.g. solutions, ointments or creams; and parenteral administration, e.g. aqueous and non-aqueous sterile injection solutions or aqueous and non-aqueous sterile suspensions. Also, the pharmaceutical compositions of the invention may include topical compositions, e.g. creams, ointments or pastes, or transdermic preparations such as patches or plasters. The pharmaceutical composition of the invention may also be prepared for vaginal or for rectal administration, e.g. rectal gel or suppository.

Generally an effective administered amount of a compound used in the invention will depend on the relative efficacy of the compound chosen, the severity of the disorder being treated, or the age, weight or mode of administration. However, active compounds will typically be administered once or more times a day, for example 1, 2, 3 or 4 times daily, with typical total daily doses in the range of from 0.01 to 100 mg/kg/day.

The compounds used in the present invention may also be administered with other drugs to provide a combination therapy. The other drugs may form part of the same composition, or be provided as a separate composition for administration at the same time or at different time.

Definitions

In the definitions of the compounds described herein the following terms have the meaning indicated:

"Alkyl" refers to a straight or branched hydrocarbon chain radical consisting of carbon and hydrogen atoms, containing no unsaturation, having one to twelve, preferably one to eight, more preferably one to six carbon atoms and which is attached to the rest of the molecule by a single bond, e.g., methyl, ethyl, n-propyl, i-propyl, n-butyl, t-butyl, n-pentyl, etc.

"Alkenyl" refers to a straight or branched hydrocarbon chain radical consisting of carbon and hydrogen atoms, containing at least one unsaturation, having two to twelve, preferably two to eight, more preferably two to six carbon atoms, and which is attached to the rest of the molecule by a single bond.

"Cycloalkyl" refers to a saturated carbocyclic ring having from three to eight, preferably three to six carbon atoms. Suitable cycloalkyl groups include, but are not limited to cycloalkyl groups such as cyclopropyl. cyclobutyl, cyclopentyl or cyclohexyl.

"Alkynyl" refers to a straight or branched hydrocarbon chain radical consisting of carbon and hydrogen atoms, containing at least one carbon-carbon triple bond, conjugated of not, having two to twelve, preferably two to eight, more preferably two to six carbon atoms, and which is attached to the rest of the molecule by a single bond, such as —CCH, —CH$_2$CCH, —CCCH$_3$, —CH$_2$CCCH$_3$, and which is attached to the rest of the molecule by a single bond.

"Aryl" refers to an aromatic hydrocarbon radical having six to ten carbon atoms such as phenyl or naphthyl.

"Aralkyl" refers to an aryl group linked to the rest of the molecule by an alkyl group such as benzyl and phenethyl.

"Heterocyclyl" refers to a stable 3- to 15-membered ring which consists of carbon atoms and from one to five heteroatoms selected from the group consisting of nitrogen, oxygen, and sulphur, preferably a 4- to 8-membered ring with one, two, three or four heteroatoms, more preferably a 5- or 6-membered ring with one, two or three heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

Unless otherwise indicated, alkyl, cycloalkyl, alkenyl, alkynyl, aryl, aralkyl and heterocyclyl radicals may be optionally substituted by one, two or three substituents such as halo, alkyl, alkenyl, alkynyl, cycloalkyl, hydroxy, alkoxy, sulfoxy, OBenzyl, OBenzoyl, carboxy, cyano, carbonyl, acyl, alkoxycarbonyl, amino, imino and nitro.

The term "alkoxycarbonyl" refers to compounds of formula —C(=O)O—, wherein the Carbon terminus is attached to the molecule and the oxygen terminus is attached to a carbon atom to form an ester functionality, i.e. MOLECULE-C(=O)O—

Said carbon atom me be part of an alkyl, alkenyl, cycloalkyl, alkynyl, aryl, aralkyl or heterocyclyl group.

EXPERIMENTAL SECTION

The examples set forth in this description detail the suitable processes for obtaining several compounds which can be assigned to formula (I). In view of said examples, it is evident and direct for a person skilled in the art to obtain the compounds which are not explicitly exemplified, by means of applying modifications of the methods set forth, characteristic of the common general knowledge of the persons skilled in the art.

Consequently, the examples set forth below must not be interpreted as limiting the scope of the present invention, but rather as an additional and more detailed explanation which guides the person skilled in the art to a deeper understanding of the invention.

The following abbreviations are used in the following examples:

| | |
|---|---|
| AcOEt | Ethyl acetate |
| AcOH | Acetic acid |
| DMSO-d$_6$ | Hexadeuterodimethyl sulfoxide |
| EtOH | Ethanol |
| Et$_2$O | Diethyl ether |
| HPLC | high pressure liquid chromatography |
| IPA | Isopropyl alcohol |
| RT | Room temperature |
| THF | Tetrahydrofuran |
| TLC | Thin layer chromatography |

The nuclear magnetic resonance spectra have been carried out in a Varian Gemini-200 apparatus.

The $^1$H-NMR spectra indicate the working frequency and the solvent used to make the spectrum. The position of the signals is indicated in δ (ppm), using the signal of the protons of the solvent as reference. The reference values are 7.24 ppm for chloroform and 2.49 ppm for deuterated dimethyl sulfoxide. Within brackets are indicated the number of protons corresponding to each signal measured by electronic integration and the type of signal using the following abbreviations: s (singlet), d (doublet), t (triplet), q (quadruplet), s.b. (signal broad). The signal assignation is indicated in some cases.

The $^{13}$C-NMR spectra indicate the working frequency and the solvent used to make the spectrum. The position of the signals is indicated in δ (ppm), using the central signal of the solvent as reference. The reference values are 77.00 ppm for chloroform and 39.50 ppm for deuterated dimethylsulfoxide.

A) Synthesis of the Relevant Compounds

Example 1

1a).—Synthesis of Ethyl formylamino-(1-methyl-piperidin-4-ilydene)-acetate

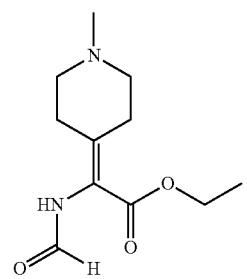

180 g (1.6 moles) of potassium tert-butoxide and 1 L of dry THF are added to a 6 L flask with 3 mouths, provided with condenser, thermometer and a calcium chloride tube. It is cooled with an ice bath and 181 ml (1.6 moles) of ethyl isocyanoacetate dissolved in 180 ml of dry THF are added dropwise, keeping the temperature below 15° C. After the addition, 187 ml (1.6 moles) of 1-methyl-4-piperidone dissolved in 187 ml of dry THF are added dropwise, keeping the temperature below 15° C. After the addition, it is allowed to reach room temperature and it is stirred for 30 minutes. 900 ml of a 1/1 AcOH/$H_2O$ solution is added, controlling that the exothermic which occurs does not exceed 45° C. After the addition, the stirring is maintained for 1 hour. The THF is eliminated under vacuum and 1 L of water is added. 350 g of sodium carbonate is added until reaching a pH between 8 and 9 and it is extracted with 5×600 ml of dichloromethane. The organic phase is dried and concentrated, obtaining 248 g of a dark brown solid which is recrystallized with 1.4 L of a 1/1 toluene/cyclohexane mixture to yield 167 g of a light brown solid (Yield: 46%).

$^1$H-NMR ($D_2O$, 200 MHz): 7.80 (s, 1H, CHO); 3.93 (q, 2H, $OCH_2$); 2.50-2.10 (m, 8H, piperidine); 1.93 (s, 3H, $NCH_3$); 0.95 (t, 3H, $CH_3$)

$^{13}$C-NMR ($D_2O$, 200 MHz): 165.81 (C=O); 163.12 (C=O); 146.88 (C=C); 117.69 (C=C); 61.94 ($OCH_2$); 54.35 and 53.98 ($NCH_2$); 43.53 ($NCH_3$); 29.08 and 28.41 ($CH_2$); 12.76 ($CH_3$)

1b).—Synthesis of Ethyl(R,S)-formylamino-[1-methyl-4-(4-methoxy-benzylsulfanyl)-piperidin-4-yl]-acetate

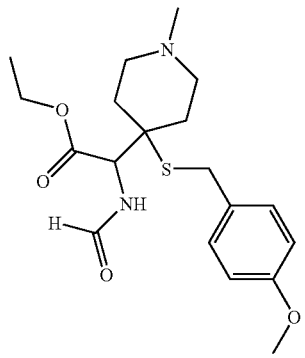

16.09 g of 55% sodium hydride in mineral oil (0.367 moles) and 300 ml of toluene are added in a 1 L flask with 3 mouths, provided with a condenser and thermometer. It is cooled at 10° C. and 56.8 ml (0.367 moles) of 4-methoxybenzylthiol dissolved in 200 ml of toluene are quickly added and it is stirred at this temperature for 5 minutes. 83.0 g (0.367 moles) of ethyl formylamino-(1-methyl-piperidin-4-ilydene)-acetate, product obtained in (1a), is added in portions, preventing the temperature for exceeding 35° C. After the addition, it is maintained at RT for 3 hours. 370 ml of 2N hydrochloric acid is added and the phases are separated. The aqueous phase is washed with 2×300 ml of toluene to eliminate impurities. The aqueous phase is taken to pH 10-11 with 2N NaOH and it is extracted with 4×300 ml of dichloromethane, which once it is dried on sodium sulfate, is filtered and concentrated. 125.7 g of a completely pure amber oil is obtained by TLC ($CH_2Cl_2$/EtOH/$NH_4OH$) and NMR. Yield: 90%

$^1$H-NMR (DMSO-$d_6$, 200 MHz): 8.70 (d, J=9.2 Hz; 1H, NH); 8.11 (s, 1H, CHO); 7.21 (d, J=8.6 Hz, 2H); 6.86 (d, J=8.6 Hz, 2H); 4.74 (d, J=9.2 Hz, 1H, CH); 4.16 (q, 2H, $OCH_2$); 3.72 (s, 3H, $OCH_3$); 3.63 (s, 2H, $SCH_2$); 2.60-2.20 (m, 4H, piperidine); 2.16 (s, 3H, $NCH_3$); 1.90-1.50 (m, 4H, piperidine); 1.24 (t, 3H, $CH_3$)

$^{13}$C-NMR (DMSO-$d_6$, 200 MHz): 169.50 (C=O); 161.23 (C=O); 158.30 (C—O); 130.26 (2C, CH); 128.67 (1C, C—$CH_2$); 113.85 (2C, CH); 60.81 ($OCH_2$); 57.01 (1C, CH); 55.04 (1C, $OCH_3$); 50.30 and 50.08 (3C, 2 $NCH_2$ and C4piperidine); 45.74 ($NCH_3$); 30.70 and 30.22 (3C, 2$CH_2$ and S—$CH_2$); 14.02 (1C, $CH_3$)

1c).—Synthesis of Ethyl(R,S)-amino-[1-methyl-4-(4-methoxy-benzylsulfanyl)-piperidin-4-yl]-acetate

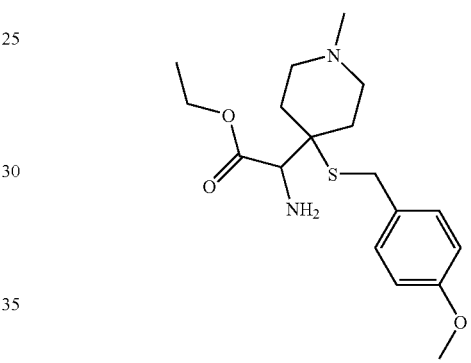

125.7 g (0.330 moles) of Ethyl(R,S)-formylamino-[1-methyl-4-(4-methoxy-benzylsulfanyl)-piperidin-4-yl]-acetate and 300 ml of a 6M EtOH/HCl solution are added to a 1 L flask and heated under reflux for 24 hours. It is concentrated to dryness and residue is dissolved in 700 ml of water and washed with 2×200 ml of AcOEt. The aqueous phase is basified with 30% $NH_4OH$ and extracted with 3×300 ml of dichloromethane. The organic phase is dried, filtered and concentrated and 109.3 g (Yield: 94%) of a completely pure amber oil are obtained by TLC ($CH_2Cl_2$/EtOH/$NH_4OH$) and NMR.

$^1$H-NMR (DMSO-$d_6$, 200 MHz): 7.21 (d, J=8.4 Hz, 2H); 6.86 (d, J=8.4 Hz, 2H); 4.12 (q, 2H, $OCH_2$); 4.10-3.90 (m, 1H, CH); 3.72 (s, 3H, $OCH_3$); 3.60 (s, 2H, $SCH_2$); 2.50 (s.b, 2H, $NH_2$); 2.40-2.20 (m, 2H, piperidine); 2.15 (s, 3H, $NCH_3$); 2.10-1.50 (m, 6H, piperidine); 1.23 (t, 3H, $CH_3$)

$^{13}$C-NMR (DMSO-$d_6$, 200 MHz): 173.32 (C=O); 158.15 (C—O); 130.11 (2C, CH); 129.36 (1C, C—$CH_2$); 113.76 (2C, CH); 61.82 (1C, CH); 59.91 ($OCH_2$); 54.99 (1C, $OCH_3$); 51.23 and 50.60 ((3C, 2 $NCH_2$ and C4piperidine); 45.90 ($NCH_3$); 30.35, 30.21 and 30.11 (3C, 2$CH_2$ and S—$CH_2$); 14.09 (1C, $CH_3$)

1d).—Synthesis of Ethyl(R,S)-acetylamino-[1-methyl-4-(4-methoxy-benzylsulfanyl)-piperidin-4-yl]-acetate

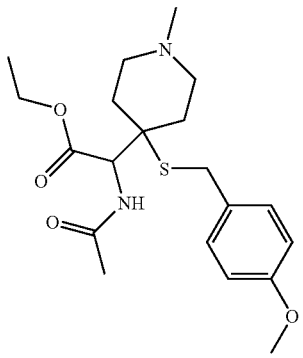

18 g (50 mmol) of Ethyl(R,S)-amino-[1-methyl-4-(4-methoxy-benzylsulfanyl)-piperidin-4-yl]-acetate, product obtained in 1c, and 300 ml of dry THF area added to a 1 L flask. It is cooled at 0° C. and 7.12 ml (50 mmol) of triethylamine are added. 3.64 ml (50 mmol) of acetyl chloride in 10 ml of dry THF are added dropwise. It is stirred for 2 hours at 0° C., it is concentrated to dryness and the residue is dissolved in 100 ml of dichloromethane and washed with 2×50 ml of a 5% sodium bicarbonate solution. The organic phase is dried, filtered and concentrated. 19.37 g (Yield: 96%) of an amber oil which crystallizes by letting it be is obtained.

$^1$H-NMR (CDCl$_3$, 200 MHz): 7.21 (d, J=8.8 Hz, 2H); 6.82 (d, J=8.8 Hz, 2H); 6.32 (d, J=9 Hz, NH); 4.78 (d, J=9 Hz, 1H, CH); 4.21 (q, 2H, OCH$_2$); 3.77 (s, 3H, OCH$_3$); 3.61-3.58 (m, 2H, SCH$_2$); 2.70-2.40 (m, 4H, piperidine); 2.28 (s, 3H, NCH$_3$); 2.00 (s, 3H, COCH$_3$); 2.10-1.60 (m, 4H, piperidine); 1.30 (t, 3H, CH$_3$)

$^{13}$C-NMR (CDCl$_3$, 200 MHz): 173.40 (C=O); 170.05 (C=O); 158.92 (C—O); 130.38 (2C, CH); 128.78 (1C, C—CH$_2$); 114.15 (2C, CH); 61.64 (OCH$_2$); 58.56 (1C, CH); 55.38 (1C, OCH$_3$); 50.91 ((3C, 2 NCH$_2$ and C4piperidine); 46.15 (NCH$_3$); 32.97, 32.05 and 31.27 (3C, 2CH$_2$ and S—CH$_2$); 23.41 (1C, CO—CH$_3$); 14.27 (1C, CH$_3$)

1e).—Synthesis of (R,S)-4-(Acetylamino-ethoxycarbonyl-methyl)-4-mercapto-1-methyl-piperidinium (II) trifluoroacetate

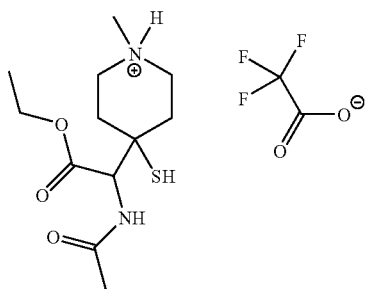

1.97 g (5 mmol) of the product obtained in 1d and 5 ml of trifluoroacetic acid are added to a 50 ml flask and heated under reflux for 20 hours. It is allowed to cool and 20 ml of water are added. It is washed with 3×50 ml of AcOEt. The aqueous phase is concentrated to dryness by azeotropically distilling the remains of water with IPA. The residue is treated with Et$_2$O and stirring and a white solid is obtained which is filtered and dried. 1.7 g are obtained (Yield: 88%)

$^1$H-NMR (DMSO-d$_6$, 200 MHz): 10.60-9.80 (s.b., 1H, CO$_2$H); 8.50-8.10 (s.b., 1H, NH); 4.52 (s.b., 1H, CH); 4.10 (q, 2H, OCH$_2$); 3.50-2.90 (m, 5H, 4Hpiperidine and SH); 2.77 (s, 3H, NCH$_3$); 2.10-1.60 (m, 7H, COCH$_3$ and 4Hpiperidine); 1.85 (t, 3H, CH$_3$)

$^{13}$C-NMR (DMSO-d$_6$, 200 MHz): 169.92 (C=O); 168.46 (C=O); 159.14 and 158.51 (CO$_2$H); 120.00 and 114.07 (CF3); 61.42 (1C, CH); 60.95 (OCH$_2$); 49.46 (2C, 2 NCH$_2$); 46.41 (1C, C4piperidine); 42.40 (NCH$_3$); 33.01 and 32.27 (2C, 2CH$_2$); 22.26 (1C, COCH$_3$); 14.01 (1C, CH$_3$)

1f).—Synthesis of Ethyl(R,S)-acetylamino-(1-methyl-4-S-nitrosomercapto-piperidin-4-yl)-acetate

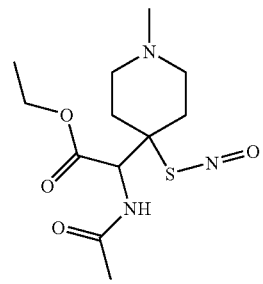

1.17 g (3 mmol) of (R,S)-4-(Acetylamino-ethoxycarbonyl-methyl)-4-mercapto-1-methyl-piperidinium trifluoroacetate (1e) are dissolved in 15 ml of 1N HCl, it is cooled externally with an ice bath for 5 min and 6 ml (6 mmol) of a 1M sodium nitrite solution are added. It is stirred at 0° C. for 5 minutes and it is taken to pH 11-12 with 2N NaOH. It is extracted with 3×30 ml of dichloromethane. The organic phase is dried, filtered and concentrated under vacuum (186 mm/Hg) and at 16° C. 650 mg of a reddish-greenish solid foam are obtained. (Yield: 72%)

$^1$H-NMR (DMSO-d$_6$, 200 MHz): 8.57 (d, J=9 Hz, NH); 5.35 (d, J=9 Hz, 1H, CH); 4.03 (q, 2H, OCH$_2$); 2.80-2.00 (m, 8H, piperidine); 2.17 (s, 3H, NCH$_3$); 1.88 (s, 3H, COCH$_3$); 1.11 (t, 3H, CH$_3$)

$^{13}$C-NMR (DMSO-d$_6$, 200 MHz): 169.87 (C=O); 169.25 (C=O); 61.16 (1C, C4piperidine); 61.00 (OCH$_2$); 59.31 (1C, CH); 50.74 and 50.61 (2C, 2NCH$_2$); 45.61 (NCH$_3$); 32.17 and 31.77 (2C, 2CH$_2$); 22.17 (1C, COCH$_3$); 13.81 (1C, CH$_3$)

1g).—Synthesis of (R,S)-4-(Acetylamino-ethoxycarbonyl-methyl)-1-methyl-4-S-nitrosomercapto-piperidinium chloride

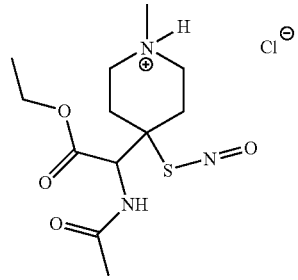

650 mg (2.14 mmol) of the product obtained in 1f) are dissolved in 50 ml of $Et_2O$ and 177 μL (2.14 mmol) of concentrated hydrochloric acid (12.076M) are added. A mixture of solid and oil is formed. 10 ml of EtOH are added until it is completely solubilized and it is concentrated to dryness, keeping the temperature under 20° C. The residue is treated with dry $Et_2O$ and stirring and a reddish-green solid precipitates which is filtered and dried. 450 mg (Yield: 62%) are thus obtained, with a 96.5% purity by HPLC.

$^1$H-NMR (DMSO-$d_6$, 200 MHz): 11.20 (s.b., HCl); 8.68 (d, J=9.6 Hz, NH); 5.24 (d, J=9.6 Hz, 1H, CH); 4.08 (q, 2H, $OCH_2$); 3.80-3.20 (m, 4H,piperidine); 3.47 (s, 3H, $NCH_3$); 3.10-2.60 (m, 4H,piperidine); 1.87 (s, 3H, $COCH_3$); 1.08 (t, 3H, $CH_3$)

$^{13}$C-NMR (DMSO-$d_6$, 200 MHz): 169.99 (C=O); 168.59 (C=O); 61.44 ($OCH_2$); 59.75 (1C, C4piperidine); 59.25 (1C, CH); 49.16 and $\overline{49}$.00 (2C, $2NCH_2$); 41.98 ($NCH_3$); 29.41 (2C, $2CH_2$); 22.20 (1C, $COCH_3$); 13.84 (1C, $CH_3$)

Starting from Ethyl(R,S)-amino-[1-methyl-4-(4-methoxy-benzylsulfanyl)-piperidin-4-yl]-acetate, obtained in 1c and substituting the acetyl chloride used in 1d with the corresponding acid chloride or sulfonyl chloride and following a process similar to those described in Examples 1d to 1f, the following products are obtained:

Example 2

Ethyl(R,S)-heptanoylamino-(1-methyl-4-S-nitrosomercapto-piperidin-4-yl)-acetate

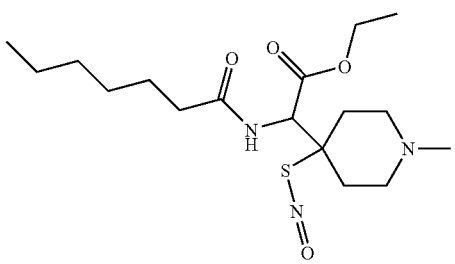

Yield last step: 66%. HPLC purity 98.8%

$^1$H-NMR (DMSO-$d_6$, 200 MHz): 8.54 (d, J=9.6 Hz, NH); 5.36 (d, J=9.6 Hz, 1H, CH); 4.04 (q, 2H, $OCH_2$); 3.04 (s.b., 2H, piperidine); 2.70-2.30 (m, 6H,piperidine); 2.43 (s, 3H, $NCH_3$); 2.16 (t, 2H, $COCH_2$); 1.43 (m, 2H, $CH_2$); 1.30-1.00 (m, 9H, $3CH_2$+$OCH_2CH_3$); 0.83 (t, 3H, $CH_3$)

$^{13}$C-NMR (DMSO-$d_6$, 200 MHz): 172.98 (C=O); 169.05 (C=O); 61.12 (1C, C4piperidine); 60.25 ($OCH_2$); 59.02 (1C, CH); 50.14 and 50.01 (2C, $2NCH_2$); 44.13 ($NCH_3$); 34.70 (1C, CO—$CH_2$), 31.11 and 30.91 (3C, $2CH_2$piperidine+$CH_2$); 28.16 (1C, $CH_2$); 25.14 (1C, $CH_2$); 21.98 (1C, $CH_2$); 13.87 and 13.80 (2C, $2CH_3$)

By a process similar to that described in 1g, the corresponding hydrochloride is obtained: (R,S)-4-(Heptanoyl-lamino-ethoxycarbonyl-methyl)-1-methyl-4-S-nitroso-mercapto-piperidinium chloride $^1$H-NMR (DMSO-$d_6$, 200 MHz): 11.20 (s.b., HCl); 8.62 (d, NH); 5.24 (d, 1H, CH); 4.09 (q, 2H, $OCH_2$); 3.10-2.60 (m, 8Hpiperidine+$NCH_3$); 2.14 (t, 2H, $COCH_2$); 1.60-1.00 (m, 4$CH_2$+$OCH_2CH_3$); 0.83 (s.b., 3H, $CH_3$)

$^{13}$C-NMR (DMSO-$d_6$, 200 MHz): 173.01 (C=O); 168.66 (C=O); 61.42 ($OCH_2$); 59.63 (1C, CH); 59.22 (1C, C4piperidine); 49.19 and 49.03 (2C, $2NCH_2$); 42.01 ($NCH_3$); 34.74 (1C, CO—$CH_2$), 30.94 (1C, $CH_2$); 29.52 and 29.33 (2C, $2CH_2$piperidine); 28.19 (1C, $CH_2$); 25.09 (1C, $CH_2$); 21.99 (1C, $CH_2$); 13.91 and 13.85 (2C, $2CH_3$)

Example 3

Ethyl(R,S)-benzoylamino-(1-methyl-4-S-nitrosomercapto-piperidin-4-yl)-acetate

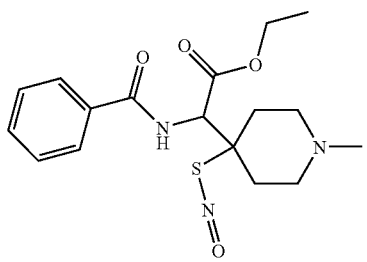

Yield last step: 5%. HPLC purity 99.3%

$^1$H-NMR (DMSO-$d_6$, 200 MHz): 8.88 (d, J=9 Hz, NH); 7.80 (d, 2H); 7.55-7.40 (m, 3H); 5.61 (d, J=9 Hz, 1H, CH); 4.08 (q, 2H, $OCH_2$); 3.43 (s.b., 2H, piperidine+$D_2O$); 2.86 (s.b., 2H, piperidine); 2.61 (s.b., 2H, piperidine); 2.27 (s.b., 5H, 2H,piperidine+$NCH_3$); 1.13 (t, 3H, $CH_3$)

$^{13}$C-NMR (DMSO-$d_6$, 200 MHz): 168.93 (C=O); 167.40 (C=O); 133.48 (1C); 131.74 (1C); 128.21 (2C); 127.87 (2C); 61.18 (1C, C4piperidine); 61.07 ($OCH_2$); 60.17 (1C, CH); 50.63 and 50.45 (2C, $2NCH_2$); 45.$\overline{10}$ ($NCH_3$); 31.96 and 31.56 (2C, $2CH_2$piperidine); 13.88 (1C, $CH_3$)

By a process similar to that described in 1g the corresponding hydrochloride is obtained: (R,S)-4-(Benzoylamino-ethoxycarbonyl-methyl)-1-methyl-4-S-nitroso-mercapto-piperidinium chloride $^1$H-NMR (DMSO-$d_6$, 200 MHz): 11.20 (s.b., HCl); 9.02 (d, NH); 7.83 (d, 2H); 7.55-7.40 (m, 3H); 5.53 (d, J=9 Hz, 1H, CH); 4.11 (q, 2H, $OCH_2$); 3.50-3.35 (m, 2H, piperidine+$D_2O$); 3.20-2.80 (m, 6H, piperidine); 2.74 (s.b., $NCH_3$); 1.13 (t, 3H, $CH_3$)

$^{13}$C-NMR (DMSO-$d_6$, 200 MHz): 168.43 (C=O); 167.51 (C=O); 133.41 (1C); 131.79 (1C); 128.20 (2C); 127.97 (2C); 61.50 ($OCH_2$); 60.29 (1C, CH); 59.31 (1C, C4piperidine); 49.27 and 49.07 (2C, $2NCH_2$); 42.05 ($NCH_3$); 29.57 and 29.27 (2C, $2CH_2$piperidine); 13.88 (1C, $CH_3$)

Example 4

Ethyl(R,S)-(4-chloro-benzoylamino)-(1-methyl-4-S-nitrosomercapto-piperidin-4-yl)-acetate

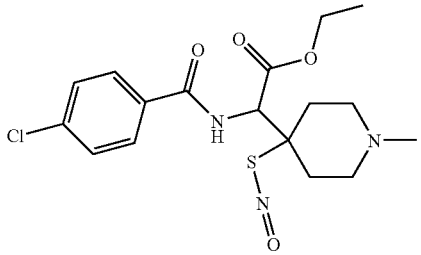

Yield last step: 77%. HPLC purity 93.4%

$^1$H-NMR (CDCl$_3$, 200 MHz): 7.66 (d, 2H); 7.38 (d, 2H); 6.92 (d, J=9 Hz, NH); 5.60 (d, J=9 Hz, 1H, CH); 4.12 (q, 2H, OCH$_2$); 2.90-2.20 (m, 8H, piperidine); 2.32 (s.b., NCH$_3$); 1.20 (t, 3H, CH$_3$)

$^{13}$C-NMR (CDCl$_3$, 200 MHz): 169.40 (C=O); 166.23 (C=O); 138.26 (1C); 131.75 (1C); 128.85 (2C); 128.49 (2C); 62.02 (OCH$_2$); 61.20 (1C, C4piperidine); 60.38 (1C, CH); 51.12 and 51.05 (2C, 2NCH$_2$); 45.83 (NCH$_3$); 33.67 (2C, 2CH$_2$piperidine); 13.88 (1C, CH$_3$)

By a process similar to that described in 1g the corresponding hydrochloride is obtained: (R,S)-4-[(4-Chloro-benzoylamino)-ethoxycarbonyl-methyl)]-1-methyl-4-S-nitrosomercapto-piperidinium chloride $^1$H-NMR (CDCl$_3$, 200 MHz): 12.40 (s.b., HCl); 7.76 (d, 2H); 7.34 (s.b., 2Hphenyl+NH); 5.60 (d, 1H, CH); 4.12 (q, 2H, OCH$_2$); 3.90-2.60 (m, 8H piperidine+NCH$_3$); 1.20 (t, 3H, CH$_3$)

$^{13}$C-NMR (CDCl$_3$, 200 MHz): 168.70 (C=O); 166.76 (C=O); 138.21 (1C); 131.41 (1C); 128.94 (2C); 128.68 (2C); 62.40 (OCH$_2$); 60.07 (1C, CH); 58.73 (1C, C4piperidine); 50.48 and 50.24 (2C, 2NCH$_2$); 43.33 (NCH$_3$); 29.82 (2C, 2CH$_2$piperidine); 13.80 (1C, CH$_3$)

Example 5

Ethyl(R,S)-(2-chloro-benzoylamino)-(1-methyl-4-S-nitrosomercapto-piperidin-4-yl)-acetate

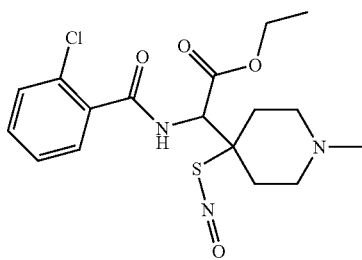

Yield last step: 91%. HPLC purity 91%

$^1$H-NMR (DMSO-d$_6$, 200 MHz): 9.32 (d, J=8.8 Hz, NH); 7.47-7.31 (m, 4H); 5.56 (d, J=8.8 Hz, 11H, CH); 4.10 (q, 2H, OCH$_2$); 3.20-2.50 (m, 8H, piperidine); 2.49 (s, NCH$_3$); 1.15 (t, 3H, CH$_3$)

$^{13}$C-NMR (DMSO-d$_6$, 200 MHz): 168.46 (C=O); 166.98 (C=O); 135.96 (1C); 130.99 (1C); 129.94 (1C); 129.45 (1C); 128.97 (1C); 126.92 (1C); 61.24 (OCH$_2$); 60.21 (1C, C4piperidine); 59.79 (1C, CH); 50.21 and 50.06 (2C, 2NCH$_2$); 44.28 (NCH$_3$); 31.31 and 31.02 (2C, 2CH$_2$piperidine); 13.84 (1C, CH$_3$)

By a process similar to that described in 1g, the corresponding hydrochloride is obtained: (R,S)-4-[(2-Chloro-benzoylamino)-ethoxycarbonyl-methyl)]-1-methyl-4-S-nitrosomercapto-piperidinium chloride $^1$H-NMR (DMSO-d$_6$, 200 MHz): 11.60 (s.b., HCl); 9.38 (d, J=8.8 Hz, NH); 7.47-7.35 (m, 4H); 5.45 (d, J=8.8 Hz, 1H, CH); 4.12 (q, 2H, OCH$_2$); 3.60-2.80 (m, 8H, piperidine); 2.72 (s, NCH$_3$); 1.15 (t, 3H, CH$_3$)

$^{13}$C-NMR (DMSO-d$_6$, 200 MHz): 168.05 (C=O); 167.03 (C=O); 135.81 (1C); 131.05 (1C); 129.95 (1C); 129.44 (1C); 128.95 (1C); 126.91 (1C); 61.54 (OCH$_2$); 60.29 (1C, CH); 59.07 (1C, C4piperidine); 49.15 and 48.98 (2C, 2NCH$_2$); 42.05 (NCH$_3$); 29.46 (2C, 2CH$_2$piperidine); 13.86 (1C, CH$_3$)

Example 6

Ethyl(R,S)-(1-methyl-4-S-nitrosomercapto-piperidin-4-yl)-[(pyridin-3-carbonyl)-amino]-acetate

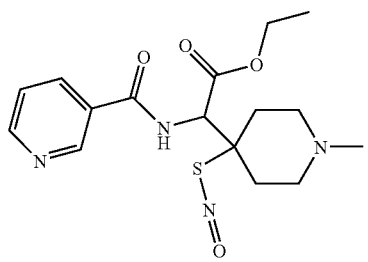

Yield last step: 76%. HPLC purity 95.2%

$^1$H-NMR (CDCl$_3$, 200 MHz): 8.96 (s.b., 1H); 8.74 (s.b., 1H); 8.04 (m, 1H); 7.39 (m, 1H); 6.99 (d, NH); 5.64 (d, 1H, CH); 4.14 (q, 2H, OCH$_2$); 3.00-2.20 (m, 8H, piperidine); 2.32 (s.b., NCH$_3$); 1.24 (t, 3H, CH$_3$)

$^{13}$C-NMR (CDCl$_3$, 200 MHz): 169.28 (C=O); 165.54 (C=O); 152.77 (1C); 148.17 (1C); 134.97 (1C); 129.19 (1C); 123.45 (1C); 62.16 (OCH$_2$); 61.20 (1C, C4piperidine); 60.51 (1C, CH); 51.11 (2C, 2NCH$_2$); 45.94 (NCH$_3$); 33.97 and 33.84 (2C, 2CH$_2$piperidine); 13.92 (1C, CH$_3$)

By a process similar to that described in 1g, the corresponding hydrochloride is obtained: (R,S)-4-{Ethoxycarbonyl-[(pyridin-3-carbonyl)-amino]-methyl}-1-methyl-4-S-nitrosomercapto-piperidinium chloride $^1$H-NMR (DMSO-d$_6$, 200 MHz): 11.60 (s.b., HCl); 9.54 (d, NH); 9.11 (s.b., 1H); 8.84 (m, 1H); 8.47 (m, 1H); 7.72 (m, 1H); 5.53 (d, 1H, CH); 4.11 (q, 2H, OCH$_2$); 3.43 (s.b., 2H piperidine); 3.00 (s.b., 6H, piperidine); 2.73 (s.b., NCH$_3$); 1.15 (t, 3H, CH$_3$)

$^{13}$C-NMR (DMSO-d$_6$, 200 MHz): 168.05 (C=O); 165.26 (C=O); 149.32 (1C); 146.38 (1C); 139.12 (1C); 130.24 (1C); 124.57 (1C); 61.61 (OCH$_2$); 60.35 (1C, CH); 59.22 (1C, C4piperidine); 49.15 and 48.99 (2C, 2NCH$_2$); 41.95 (NCH$_3$); 29.46 and 29.00 (2C, 2CH$_2$piperidine); 13.84 (1C, CH$_3$)

Example 7

Ethyl(R,S)-benzenesulfonylamino-(1-methyl-4-S-nitrosomercapto-piperidin-4-yl)-acetate

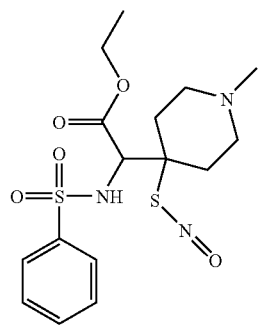

Yield last step: 99%. HPLC purity 96%

$^1$H-NMR (DMSO-d$_6$, 200 MHz): 8.75 (s.b., NH); 7.76-7.53 (m, 5H); 4.61 (s.b., 1H, CH); 3.58 (q, 2H, OCH$_2$); 2.80-2.00 (m, 8H, piperidine); 2.15 (s, NCH$_3$); 0.83 (t, 3H, CH$_3$)

$^{13}$C-NMR (DMSO-d$_6$, 200 MHz): 168.12 (C=O); 140.36 (1C); 132.65 (1C); 128.99 (2C); 126.57 (2C); 63.58 (1C, CH); 60.86 (OCH$_2$+C4piperidine); 50.63 and 50.56 (2C, 2NCH$_2$); 45.61 (NCH$_3$); 31.61 (2C, 2CH$_2$piperidine); 13.39 (1C, CH$_3$)

By a process similar to that described in 1g, the corresponding hydrochloride is obtained: (R,S)-4-(Benzenesulfonylamino-ethoxycarbonyl-methyl)-1-methyl-4-S-nitrosomercapto-piperidinium chloride $^1$H-NMR (DMSO-d$_6$, 200 MHz): 11.40 (s.b., HCl); 8.85 (d, NH); 7.76-7.53 (m, 5H); 4.47 (d, 1H, CH); 3.67 (q, 2H, OCH$_2$); 3.50-2.60 (m, 8H, piperidine); 2.70 (s, NCH$_3$); 0.86 (t, 3H, CH$_3$)

$^{13}$C-NMR (DMSO-d$_6$, 200 MHz): 167.47 (C=O); 140.17 (1C); 132.78 (1C); 129.05 (2C); 126.63 (2C); 64.21 (1C, CH); 61.35 (OCH$_2$); 58.92 (1C, C4piperidine); 49.08 and 48.86 (2C, 2NCH$_2$); 42.03 (NCH$_3$); 29.67 and 28.81 (2C, 2CH$_2$piperidine); 13.43 (1C, CH$_3$)

Example 8

Ethyl(R,S)-(1-methyl-4-S-nitrosomercapto-piperidin-4-yl)-(4-nitro-benzenesulfonylamino)-acetate

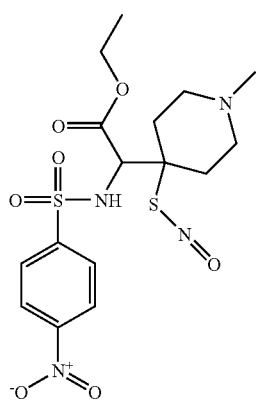

Yield last step: 46%. HPLC purity: 96.2%

$^1$H-NMR (DMSO-d$_6$, 200 MHz): 8.39 (d, J=8.8 Hz, 2H); 8.01 (d, J=8.8 Hz, 2H); 4.68 (s, 1H, CH); 3.66 (q, 2H, OCH$_2$); 3.00-2.20 (m, 8H, piperidine); 2.32 (s, NCH$_3$); 0.83 (t, 3H, CH$_3$).

$^{13}$C-NMR (DMSO-d$_6$, 200 MHz): 167.79 (C=O); 149.68 (1C); 145.89 (1C); 128.29 (2C); 124.38 (2C); 63.75 (1C, CH); 61.26 (OCH$_2$); 60.27 (1C; C4piperidine); 50.12 and 50.01 (2C, 2NCH$_2$); 44.46 (NCH$_3$); 31.14 and 30.96 (2C, 2CH$_2$piperidine); 13.40 (1C, CH$_3$).

Example 9

Ethyl(R,S)-(1-methyl-4-S-nitrosomercapto-piperidin-4-yl)-(4-methoxy-benzenesulfonylamino)-acetate

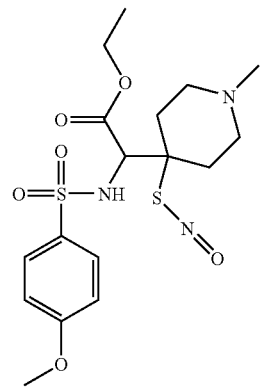

Yield last step: 92%. HPLC purity 97.7%

$^1$H-NMR (DMSO-d$_6$, 200 MHz): 8.55 (s.b., 1H, NH); 7.67 (d, J=7.8 Hz, 2H); 7.05 (d, J=7.8 Hz, 2H); 4.57 (s, 1H, CH); 3.80 (s, 3H, OCH$_3$); 3.62 (q, 2H, OCH$_2$); 2.80-2.00 (m, 8H, piperidine); 2.14 (s, NCH$_3$); 0.86 (t, 3H, CH$_3$).

$^{13}$C-NMR (DMSO-d$_6$, 200 MHz): 168.37 (C=O); 162.42 (1C, C—O); 132.04 (1C, C—SO$_2$); 128.89 (2C); 114.09 (2C); 63.58 (1C, CH); 60.95 and 60.87 (OCH$_2$+C4piperidine); 55.67 (1C, OCH$_3$); 50.70 and 50.64 (2C, 2NCH$_2$); 45.64 (NCH$_3$); 31.69 (2C, 2CH$_2$piperidine); 13.41 (1C, CH$_3$).

Example 10

Ethyl(R,S)-(4-methyl-benzenesulfonylamino)-(1-methyl-4-S-nitroso-mercapto-piperidin-4-yl)-acetate

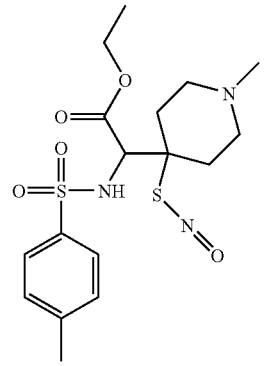

Yield last step: 93%. HPLC purity 94.8%

$^1$H-NMR (DMSO-d$_6$, 200 MHz): 8.65 (s.b., 1H, NH); 7.63 (d, J=8 Hz, 2H); 7.34 (d, J=8 Hz, 2H); 4.59 (s, 1H, CH); 3.62 (q, 2H, OCH$_2$); 2.80-2.00 (m, 8H, piperidine); 2.35 (s, 3H, CH$_3$); 2.14 (s, NCH$_3$); 0.84 (t, 3H, CH$_3$)

$^{13}$C-NMR (DMSO-d$_6$, 200 MHz): 168.20 (C=O); 142.99 (1C, C—C); 137.50 (1C, C—SO$_2$); 129.36 (2C); 126.65 (2C); 63.53 (1C, CH); 60.88 and 60.86 (OCH$_2$+C4piperidine); 50.63 and 50.56 (2C, 2NCH$_2$); 45.58 (NCH$_3$); 31.58 (2C, 2CH$_2$piperidine); 20.91 (1C, CH$_3$); 13.33 (1C, CH$_3$)

Example 11

Ethyl(R,S)-(2-chloro-benzenesulfonylamino)-(1-methyl-4-S-nitroso-mercapto-piperidin-4-yl)-acetate

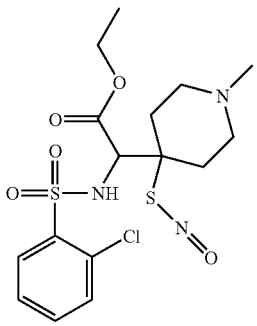

Yield last step: 80%. HPLC purity: 89.3%

$^1$H-NMR (DMSO-d$_6$, 200 MHz): 8.90 (s.b., NH); 7.92 (d, 1H); 7.64-7.42 (m, 3H); 4.69 (s, 1H, CH); 3.80 (q, 2H, OCH$_2$); 2.80-2.00 (m, 8H, piperidine); 2.17 (s, NCH$_3$); 0.94 (t, 3H, CH$_3$).

$^{13}$C-NMR (DMSO-d$_6$, 200 MHz): 168.23 (C=O); 137.37 (1C, C—Cl); 134.38 (1C, C—SO$_2$); 131.68 (1C); 130.90 (1C); 130.80 (1C); 127.58 (1C); 63.78 (1C, CH); 61.14 (OCH$_2$); 60.94 (1C, C4piperidine); 50.62 and 50.52 (2C, 2NCH$_2$); 45.52 (NCH$_3$); 31.56 (2C, 2CH$_2$piperidine); 13.52 (1C, CH$_3$).

Example 12

Ethyl(R,S)-(3-chloro-benzenesulfonylamino)-(1-methyl-4-S-nitroso-mercapto-piperidin-4-yl)-acetate

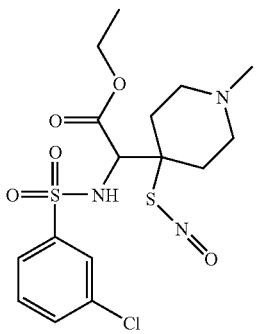

Yield last step: 76%. HPLC purity 99.9%

$^1$H-NMR (DMSO-d$_6$, 200 MHz): 7.76-7.53 (m, 4H); 4.63 (s.b., 1H, CH); 3.63 (q, 2H, OCH$_2$); 2.80-2.20 (m, 8H, piperidine); 2.25 (s, NCH$_3$); 0.86 (t, 3H, CH$_3$)

$^{13}$C-NMR (DMSO-d$_6$, 200 MHz): 167.93 (C=O); 142.25 (1C); 133.69 (1C); 132.65 (1C); 131.15 (1C); 126.26 (1C); 125.27 (1C); 63.71 (1C, CH); 61.14 (OCH$_2$); 60.57 (C4piperidine); 50.34 and 50.25 (2C, 2NCH$_2$); 45.98 (NCH$_3$); 31.44 and 31.21 (2C, 2CH$_2$piperidine); 13.40 (1C, CH$_3$)

Example 13

Ethyl(R,S)-(4-chloro-benzenesulfonylamino)-(1-methyl-4-S-nitroso-mercapto-piperidin-4-yl)-acetate

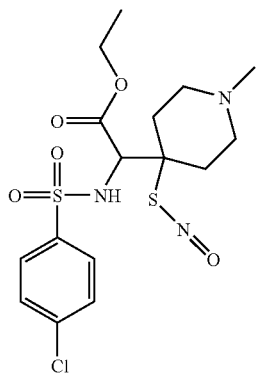

Yield last step: 88%. HPLC purity 95.8%

$^1$H-NMR (DMSO-d$_6$, 200 MHz): 7.76 (d, J=9 Hz, 2H); 7.62 (d, J=9 Hz, 2H); 4.63 (s, 1H, CH); 3.66 (q, 2H, OCH$_2$); 2.80-2.00 (m, 8H, piperidine); 2.16 (s, NCH$_3$); 0.86 (t, 3H, CH$_3$)

$^{13}$C-NMR (DMSO-d$_6$, 200 MHz): 168.09 (C=O); 139.28 (1C, C—Cl); 137.65 (1C, C—SO$_2$); 129.11 (2C); 128.60 (2C); 63.67 (1C, CH); 61.00 (OCH$^2$); 60.79 (1C, C4piperidine); 50.62 and 50.55 (2C, 2NCH$_2$); 45.53 (NCH$_3$); 31.72 (2C, 2CH$_2$piperidine); 13.36 (1C, CH$_3$)

By a process similar to that described in 1g, the corresponding hydrochloride is obtained: (R,S)-4-(4-Chloro-benzenesulfonylamino-ethoxycarbonyl-methyl)-1-methyl-4-S-nitrosomercapto-piperidinium chloride $^1$H-NMR (DMSO-d$_6$, 200 MHz): 8.90 (s.b., 1H, NH); 7.76 (d, J=8 Hz, 2H); 7.65 (d, J=8 Hz, 2H); 4.58 (s.b., 1H, CH); 3.70 (q, 2H, OCH$_2$); 3.40-2.60 (m, 8H, piperidine); 2.70 (s, NCH$_3$); 0.88 (t, 3H, CH$_3$)

$^{13}$C-NMR (DMSO-d$_6$, 200 MHz): 167.51 (C=O); 139.08 (1C, C—Cl); 137.71 (1C, C—SO$_2$); 129.19 (2C); 128.63 (2C); 63.00 (1C, CH); 61.42 (OCH$_2$); 58.92 (1C, C4piperidine); 49.04 and 48.88 (2C, 2NCH$_2$); 42.05 (NCH$_3$); 29.61 and 29.11 (2C, 2CH$_2$piperidine); 13.36 (1C, CH$_3$)

Example 14

(R,S)-4-(2-Fluoro-benzenesulfonylamino)-(1-methyl-4-S-nitroso-mercapto-piperidin-4-yl)-acetate

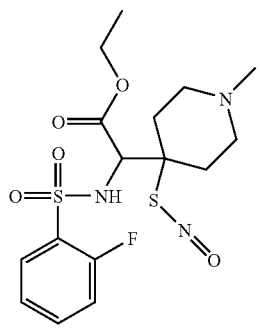

By a process similar to that described in 1g, the corresponding hydrochloride is obtained: (R,S)-4-(2-Fluoro-benzenesulfonylamino-ethoxycarbonyl-methyl)-1-methyl-4-S-nitrosomercapto-piperidinium chloride Yield last step: 89%. HPLC purity 95.4%

$^1$H-NMR (DMSO-d$_6$, 200 MHz): 9.10 (s.b., NH); 7.80-7.65 (m, 2H); 7.44-7.30 (m, 2H); 4.68 (s, 1H, CH); 3.80 (q, 2H, OCH$_2$); 3.10 (s.b., 2H, piperidine); 2.75-2.40 (m, 6H, piperidine); 2.48 (s, NCH$_3$); 0.94 (t, 3H, CH$_3$)

$^{13}$C-NMR (DMSO-d$_6$, 200 MHz): 167.88 (C=O); 160.60 and 155.54 (1C, C—F); 135.81 and 135.64 (1C, C—SO$_2$); 129.90 (1C); 128.11 and 127.83 (1C); 124.86 and 124.78 (1C); 117.29 and 116.87 (1C); 63.86 (1C, CH); 61.38 (OCH$_2$); 59.85 (1C, C4piperidine); 49.63 (2C, 2NCH$_2$); 43.47 (NCH$_3$); 30.48 and 30.21 (2C, 2CH$_2$piperidine); 13.50 (1C, CH$_3$)

Example 15

Ethyl(R,S)-(4-fluoro-benzenesulfonylamino)-(1-methyl-4-S-nitroso-mercapto-piperidin-4-yl)-acetate

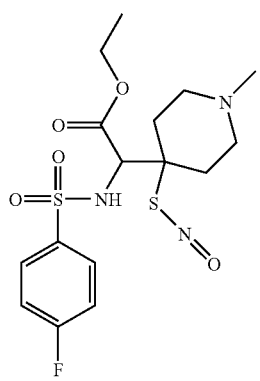

Yield last step: 95%. HPLC purity 99.4%

$^1$H-NMR (DMSO-d$_6$, 200 MHz): 8.80 (s.b., NH); 7.84-7.77 (m, 2H); 7.44-7.36 (m, 2H); 4.61 (s, 1H, CH); 3.66 (q, 2H, OCH$_2$); 2.75-2.00 (m, 8H, piperidine); 2.15 (s, NCH$_3$); 0.86 (t, 3H, CH$_3$)

$^{13}$C-NMR (DMSO-d$_6$, 200 MHz): 168.15 (C=O); 166.76 and 161.77 (1C, C—F); 136.83 and 136.76 (1C, C—SO$_2$); 129.80 and 129.61 (2C); 116.37 and 115.92 (2C); 63.62 (1C, CH); 60.99 (OCH$_2$); 60.88 (1C, C4piperidine); 50.64 and 50.56 (2C, 2NCH$_2$); 45.61 (NCH$_3$); 31.73 and 31.65 (2C, 2CH$_2$piperidine); 13.42 (1C, CH$_3$)

By a process similar to that described in 1g, the corresponding hydrochloride is obtained: (R,S)-4-(4-Fluoro-benzenesulfonylamino-ethoxycarbonyl-methyl)-1-methyl-4-S-nitrosomercapto-piperidinium chloride $^1$H-NMR (DMSO-d$_6$, 200 MHz): 8.80 (s.b., NH); 7.81 (s.b., 2H); 7.40 (s.b., 2H); 4.56 (s.b., 1H, CH); 3.69 (q, 2H, OCH$_2$); 3.60-2.60 (m, 8H, piperidine); 2.68 (s, NCH$_3$); 0.88 (t, 3H, CH$_3$)

$^{13}$C-NMR (DMSO-d$_6$, 200 MHz): 167.01 (C=O); 166.85 and 161.86 (1C, C—F); 136.70 and 136.64 (1C, C—SO$_2$); 129.91 and 129.72 (2C); 116.46 and 116.01 (2C); 63.66 (1C, CH); 61.44 (OCH$_2$); 59.02 (1C, C4piperidine); 49.10 and 48.92 (2C, 2NCH$_2$); 42.12 (NCH$_3$); 29.71 and 29.16 (2C, 2CH$_2$piperidine); 13.46 (1C, CH$_3$)

Example 16

Ethyl(R,S)-(2,4-difluoro-benzenesulfonylamino)-(1-methyl-4-S-nitroso mercapto-piperidin-4-yl)-acetate

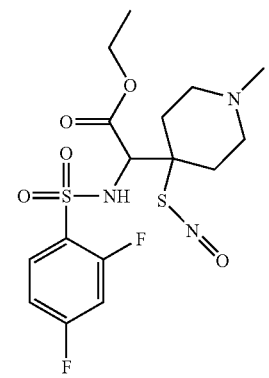

Yield last step: 52%. HPLC purity 98.4%

$^1$H-NMR (DMSO-d$_6$, 200 MHz): 7.78 (m, 1H); 7.42 (m, 1H); 7.18 (m, 1H); 4.64 (s, 1H, CH); 3.76 (q, 2H, OCH$_2$); 2.75-2.00 (m, 8H, piperidine); 2.15 (s, NCH$_3$); 0.95 (t, 3H, CH$_3$)

$^{13}$C-NMR (DMSO-d$_6$, 200 MHz): 168.97 (C=O); 168.76 and 161.56 (1C, C—F); 161.30 and 156.45 (1C, C—F); 131.96 and 131.74 (1C, CH); 126.33 and 126.26 (1C, C—SO$_2$); 111.97 and 111.54 (1C, CH); 106.04, 105.51 and 104.99 (1C, C—H); 64.28 (1C, CH); 61.47 (OCH$_2$); 60.86 (1C, C4piperidine); 50.84 and 50.76 (2C, 2NCH$_2$); 45.71 (NCH$_3$); 31.87 and 31.81 (2C, 2CH$_2$piperidine); 13.57 (1C, CH$_3$)

By a process similar to that described in 1g the corresponding hydrochloride is obtained: (R,S)-4-(2,4-Difluoro-benzenesulfonylamino-ethoxycarbonyl-methyl)-1-methyl-4-S-nitrosomercapto-piperidinium chloride $^1$H-NMR (DMSO-d$_6$, 200 MHz): 11.50 (s.b. 1H, HCl); 9.20 (s.b., NH); 7.82 (m, 1H); 7.52 (m, 1H); 7.24 (m, 1H); 4.60 (s, 1H, CH); 3.90 (q, 2H, OCH$_2$); 3.50-2.60 (m, 8H, piperidine); 2.71 (s, NCH$_3$); 0.99 (t, 3H, CH$_3$)

$^{13}$C-NMR (DMSO-d$_6$, 200 MHz): 167.62 (C=O); 167.84; 167.62; 162.79 and 162.55 (1C, C—F); 161.60; 161.34;

156.49 and 156.23 (1C, C—F); 132.17 and 131.96 (1C, CH); 124.92 and 124.57 (1C, C—SO$_2$); 112.38 and 112.00 (1C, CH); 106.34; 105.83 and 105.31 (1C, C—H); 64.37 (1C, CH); 61.76 (OCH$_2$); 59.07 (1C, C4piperidine); 49.15 and 48.91 (2C, 2NCH$_2$); 42.01 (NCH$_3$); 29.87 and 28.94 (2C, 2CH$_2$piperidine); 13.57 (1C, CH$_3$)

Example 17 a) Synthesis of (R,S)-4-(Ethoxycarbonyl-formylamino-methyl)-4-mercapto-1-methyl-piperidinium trifluoroacetate

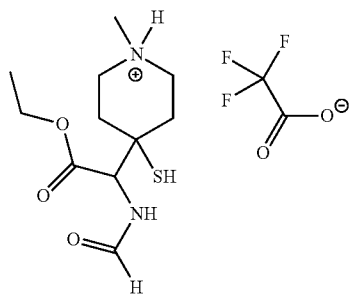

The product of the title is obtained starting from the product obtained in example 1b and proceeding as described in example 1e.

$^1$H-NMR (DMSO-d$_6$, 200 MHz): 10.20-9.80 (s.b., 1H, CO$_2$H); 8.80-8.40 (s.b., 1H, NH); 8.13 (s, 1H, CHO); 4.60 (d, 1H, CH); 4.14 (q, 2H, OCH$_2$); 3.50-3.10 (m, 5H, 4Hpiperidine and SH); 2.79 (s, 3H, NCH$_3$); 2.10-1.70 (m, 4Hpiperidine); 1.21 (t, 3H, CH$_3$)

$^{13}$C-NMR (DMSO-d$_6$, 200 MHz): 168.46 (C=O); 161.44 (C=O); 158.99 and 158.27 (CO$_2$H); 118.84 and 113.03 (CF3); 62.07 (1C, CH); 61.19 (OCH$_2$); 49.53 and 49.38 (2C, 2 NCH$_2$); 46.46 (1C, C4piperidine); 42.44 (NCH$_3$); 33.12 and 32.50 (2C, 2CH$_2$); 13.98 (1C, CH$_3$)

b) Synthesis of Ethyl(R,S)-formylamino-(1-methyl-4-S-nitrosomercapto-piperidin-4-yl)-acetate

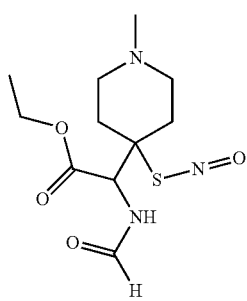

The product of the title is obtained starting from (R,S)-4-(Ethoxycarbonyl-formylamino-methyl)-4-mercapto-1-methyl-piperidinium trifluoroacetate and proceeding as described in example 1f.

$^1$H-NMR (DMSO-d$_6$, 200 MHz): 8.90 (d, NH); 8.09 (s, 1H, CHO); 5.35 (d, J=9.6 Hz, 1H, CH); 4.05 (q, 2H, OCH$_2$); 2.80-2.00 (m, 8H,piperidine); 2.17 (s, 3H, NCH$_3$); 1.15 (t, 3H, CH$_3$)

$^{13}$C-NMR (DMSO-d$_6$, 200 MHz): 168.77 (C=O); 161.38 (C=O); 61.22 (1C, C4piperidine); 60.98 (OCH$_2$); 57.94 (1C, CH); 50.72 and 50.62 (2C, 2NCH$_2$); 45.64 (NCH$_3$); 32.31 and 32.14 (2C, 2CH$_2$); 13.80 (1C, CH$_3$)

By a process similar to that described in 1g, the corresponding hydrochloride is obtained: (R,S)-4-(Ethoxycarbonyl-formylamino-methyl)-1-methyl-4-S-nitroso-mercapto-piperidinium chloride $^{13}$C-NMR (DMSO-d$_6$, 200 MHz): 168.16 (C=O); 161.53 (C=O); 61.67 (OCH$_2$); 59.11 (1C, CH); 58.48 (1C, C4piperidine); 48.94 (2C, 2NCH$_2$); 41.97 (NCH$_3$); 29.73 and 29.37 (2C, 2CH$_2$); 13.81 (1C, CH$_3$)

Example 18 a) Synthesis of (R,S)-4-[Ethoxycarbonyl-(2,2,2-trifluoro-acetylamino)-methyl]-4-mercapto-1-methyl-piperidinium trifluoroacetate

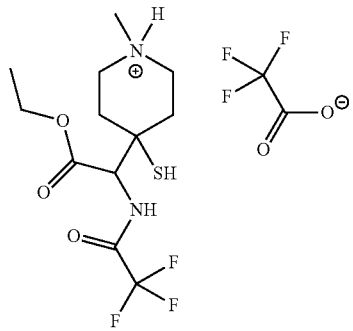

The product of the title is obtained starting from the product obtained in Example 1c and proceeding as described in Example 1 e.

$^1$H-NMR (DMSO-d$_6$, 200 MHz): 9.84 (d, 1H, NH); 4.72 (d, 1H, CH); 4.17 (q, 2H, OCH$_2$); 3.70-3.10 (m, 5H, 4Hpiperidine and SH); 2.76 (s, 3H, NCH$_3$); 2.20-1.80 (m, 4Hpiperidine); 1.21 (t, 3H, CH$_3$)

b) Synthesis of Ethyl(R,S)-(1-methyl-4-S-nitrosomercapto-piperidin-4-yl)-(2,2,2-trifluoro-acetylamino)-acetate

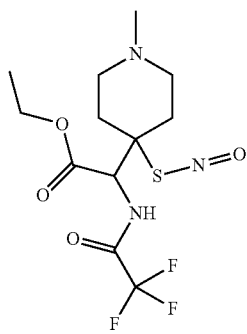

The product of the title is obtained starting from (R,S)-4-[Ethoxycarbonyl-(2,2,2-trifluoro-acetylamino)-methyl]-4-mercapto-1-methyl-piperidinium trifluoroacetate and proceeding as described in Example 1f.

Yield: 84% HPLC purity 95%

$^1$H-NMR (CDCl$_3$, 200 MHz): 7.10 (d, NH); 5.37 (d, 1H, CH); 4.15 (q, 2H, OCH$_2$); 2.90-2.20 (m, 8H,piperidine); 2.33 (s, 3H, NCH$_3$); 1.24 (t, 3H, CH$_3$)

$^{13}$C-NMR (CDCl$_3$, 200 MHz): 167.89 (C=O); 159.00 (C=O); 118.42 and 112.69 (CF$_3$); 62.61 (OCH$_2$); 60.83 (1C, C4piperidine); 60.54 (1C, CH); 50.99 (2C, 2NCH$_2$); 45.91 (NCH$_3$); 33.85 and 33.75 (2C, 2CH$_2$); 13.87 (1C, CH$_3$)

By a process similar to that described in 1g, the corresponding hydrochloride is obtained:

$^1$H-NMR (CDCl$_3$, 200 MHz): 12.20 (HCl); 7.94 (d, NH); 5.50 (d, 1H, CH); 4.22 (q, 2H, OCH$_2$); 3.90-2.20 (m, 8H,piperidine); 2.86 (s, 3H, NCH$_3$); 1.24 (t, 3H, CH$_3$)

Example 19 a) Synthesis of Benzyl amino-[1-methyl-4-(4-methoxy-benzylsulfanyl)-piperidin-4-yl]-acetate

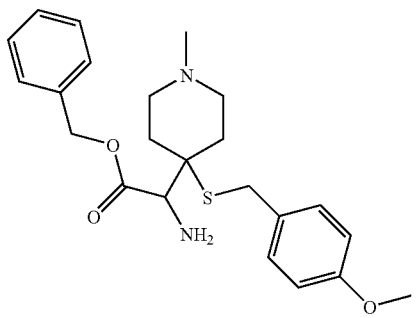

The product of the title is obtained starting from the product obtained in Example 1c by treatment with benzyl alcohol at 100° C.

$^1$H-NMR (DMSO-d$_6$, 200 MHz): 7.41-7.33 (m,5H); 7.10 (d, J=8.8 Hz, 2H); 6.79 (d, J=8.8 Hz, 2H); 5.14 (s, 2H, OCH$_2$Ph); 3.70 (s, 3H, OCH$_3$); 3.60-3.40 (m, CH+SCH$_2$); 2.50 (s.b., 2H, NH$_2$); 2.40-2.20 (m, 2H, piperidine); 2.15 (s, 3H, NCH$_3$); 2.10-1.50 (m, 6H, piperidine)

$^{13}$C-NMR (DMSO-d$_6$, 200 MHz): 173.34 (C=O); 158.13 (C—O); 135.90 (1C, C—CH$_2$O); 130.15 (2C); 129.28 (1C C—CH$_2$S); 128.41-128.07 (5C); 113.73 (2C, CH); 65.67 (O CH$_2$); 61.93 (1C, CH); 54.99 (1C, OCH$_3$); 51.20 and 50.58 (3C, 2NCH$_2$ and C4piperidine); 45.86 (NCH$_3$); 30.29 and 30.15 (3C, 2CH$_2$ and S—CH$_2$)

b) Synthesis of Benzyl(R,S)-acetylamino-(1-methyl-4-S-nitrosomercapto-piperidin-4-yl)-acetate

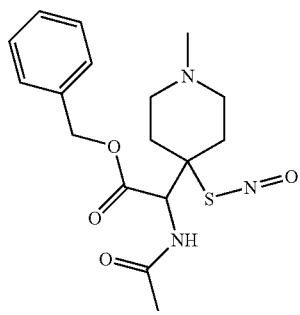

The product of the title is obtained starting from the product obtained in 19a and following the processes described in 1d to 1f.

$^1$H-NMR (CDCl$_3$, 200 MHz): 7.34-7.21 (m, 5H); 6.64 (d, NH); 5.50 (d, 1H, CH); 5.02 (s, 2H, OCH$_2$); 2.90-2.20 (m, 8H, piperidine); 2.36 (s, NCH$_3$); 2.08 (s, 3H, COCH$_3$)

$^{13}$C-NMR (CDCl$_3$, 200 MHz): 170.23 (CO); 169.41 (C=O); 134.46 (1C); 128.49 (5C); 67.49 (OCH$_2$); 60.43 (C4piperidine); 59.78 (1C, CH); 51.02 and 50.87 (2C, 2NCH$_2$); 45.49 (NCH$_3$); 33.07 and 32.59 (2C, 2CH$_2$piperidine); 23.03 (1C, CH$_3$)

Example 20 a) Synthesis of Ethyl amino-[1-methyl-4-(4-methoxy-benzylsufanil)-piperidin-4-yl]-acetate

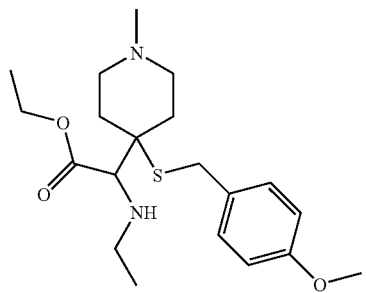

Starting from 10 g (28.37 mmol) of the product obtained in Example 1c by reductive amination with acetaldehyde (1.4 g; 31.2 mmol) and sodium cyanoborohydride (1.8 g; 30 mmol) in ethanol and after subjecting the crude reaction product to column chromatography on silica gel and eluting with dichloromethane, 5.4 g of the product of the title are obtained after concentrating to dryness.

$^1$H-NMR (DMSO-d$_6$, 200 MHz): 7.20 (d, J=8.4 Hz, 2H); 6.85 (d, J=8.8 Hz, 2H); 4.15 (q, 2H, OCH$_2$); 3.72 (s, 3H, OCH$_3$); 3.62 (d, 2H, SCH$_2$); 3.36-3.20 (m, 2H, NH+CH); 2.60-2.20 (m, 6H, 4Hpiperidine+NCH$_2$); 2.14 (s, 3H, NCH$_3$); 2.10-1.50 (m, 4H, piperidine); 1.23 (t, 3H, CH$_3$); 1.00 (t, 3H, CH$_3$)

$^{13}$C-NMR (DMSO-d$_6$, 200 MHz): 173.21 (C=O); 158.17 (C—O); 130.09 (2C, CH); 129.31 (1C, C—CH$_2$); 113.77 (2C, CH); 68.72 (1C, CH); 59.91 (OCH$_2$); 55.00 (1C, OCH$_3$); 50.54 and 50.20 (3C, 2NCH$_2$ and C4piperidine); 45.92 (NCH$_3$); 42.48 (HN—CH$_2$); 30.77; 30.43 and 30.28 (3C, 2CH$_2$ and S—CH$_2$); 15.21 (1C, CH$_3$); 14.20 (1C, CH$_3$)

b) Synthesis of Ethyl(acetyl-ethyl-amino)-[1-methyl-4-(4-methoxy-benzylsulfanyl)-piperidin-4-yl]-acetate

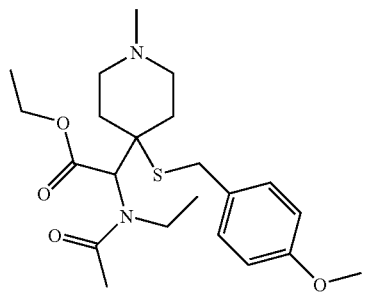

3.8 g (10 mmol) of the product obtained in a) are subjected to reflux in 50 ml of acetic anhydride for 16 hours. It is concentrated to dryness and the residue is dissolved in 50 ml of water and basified with 2N NaOH. It is extracted with 3×100 ml of dichloromethane. The extracts are dried and concentrated and the residue is chromatographed on silica gel. 1.7 g of the product of the title is obtained by eluting with 90/10/1% $CH_2Cl_2$/EtOH/$NH_4OH$.

$^1$H-NMR (DMSO-$d_6$, 200 MHz): 7.20 (d, J=8.4 Hz, 2H); 6.86 (d, J=8.8 Hz, 2H); 5.02 (s.b., 1H, CH); 4.10 (m, 2H, $OCH_2$+NH); 3.72 (s, 3H, $OCH_3$); 3.62 (s.b., 2H, $SCH_2$); 3.44 (q, 2H, $NCH_2$); 2.60-2.20 (m, 4H, 4Hpiperidine); 2.14 (s, 3H, $NCH_3$); 2.10 (s, 3H, $COCH_3$); 2.00-1.50 (m, 4H, piperidine); 1.20 (t, 3H, $CH_3$); 1.05 (t, 3H, $CH_3$)

$^{13}$C-NMR (DMSO-$d_6$, 200 MHz): 171.29 (C=O); 168.54 (C=O); 158.25 (C—O); 130.18 (2C, CH); 128.96 (1C, C—$CH_2$); 113.85 (2C, CH); 60.62 (1C, CH); 60.27 ($OCH_2$); 55.02 (1C, $OCH_3$); 52.56 (1C, C4piperidine); 50.54 and 50.39 (2C, 2$NCH_2$); 45.76 ($NCH_3$); 42.57 (HN—$CH_2$); 30.73 and 30.57 (3C, $2CH_2$ and S—$CH_2$); 21.39 (1C, $COCH_3$); 14.65 (1C, $CH_3$); 13.88 (1C, $CH_3$)

c) Synthesis of Ethyl(R,S)-(acetyl-ethyl-amino)-(1-methyl-4-S-nitrosomercapto-piperidin-4-yl)-acetate

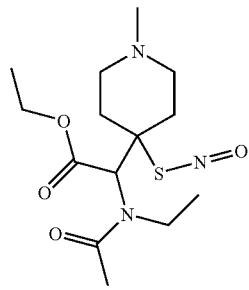

The product of the title is obtained starting from the product obtained in b) and following the processes described in 1e and 1f.

$^1$H-NMR (CDCl$_3$, 200 MHz): 5.28 (s.b., 1H, CH); 4.10 (q, 2H, $OCH_2$); 3.80-3.20 (m, 2H, $NCH_2$); 3.10-2.20 (m, 8H, piperidine); 2.39 (s, 3H, $NCH_3$); 2.17 (s, 31H, $COCH_3$); 1.28-1.14 (m, 6H, 2$CH_3$)

$^{13}$C-NMR (CDCl$_3$, 200 MHz): 172.14 (C=O); 168.12 (C=O); 64.97 (1C, CH); 62.29 (1C, C4piperidine); 61.13 (O$CH_2$); 51.35 and 50.92 (2C, 2$NCH_2$); 50.25 (1C, $NCH_2$); 45.33 ($NCH_3$); 32.97 and 31.23 (2C, $2CH_2$); 21.57 (1C, $COCH_3$); 14.33 (1C, $CH_3$); 13.89 (1C, $CH_3$)

The following products are obtained by following a process similar to that described in example 1 but substituting 1-methyl-4-piperidone with 1-ethyl-4-piperidone or 1-benzyl-4-piperidone in step a):

Example 21

Synthesis of Ethyl(R,S)-acetylamino-(1-ethyl-4-S-nitrosomercapto-piperidin-4-yl)-acetate

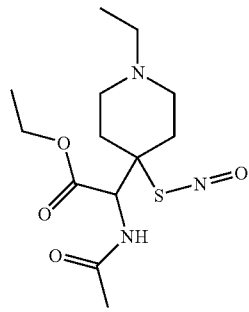

Yield last step: 51%; HPLC purity: 89.3%

$^1$H-NMR (DMSO-$d_6$, 200 MHz): 8.59 (d, J=9.2 Hz, NH); 5.36 (d, J=9.2 Hz, 1H, CH); 4.05 (q, 2H, $OCH_2$); 3.00-2.10 (m, 10H, 8H, piperidine+$NCH_2$); 1.88 (s, 3H, $COCH_3$); 1.14-0.98 (m, 6H, 2$CH_3$)

$^{13}$C-NMR (DMSO-$d_6$, 200 MHz): 169.68 (C=O); 169.18 (C=O); 61.45 (1C, C4piperidine); 61.02 ($OCH_2$); 59.23 (1C, CH); 51.36 (1C, $NCH_2$); 48.22 and 48.07 (2C, 2$NCH_2$); 31.93 and 31.42 (2C, 2$CH_2$); 22.18 (1C, $COCH_3$); 13.79 (1C, $CH_3$); 11.53 (1C, $CH_3$);

By a process similar to that described in 1g the corresponding hydrochloride is obtained: (R,S)-(acetylamino-ethoxycarbonyl-methyl)-1-ethyl-4-S-nitrosomercapto-piperidinium chloride $^1$H-NMR (DMSO-$d_6$, 200 MHz): 11.30 (HCl); 8.66 (d, NH); 5.22 (d, J=9.2 Hz, 1H, CH); 4.05 (q, 2H, $OCH_2$); 3.60-2.60 (m, 10H, 8H, piperidine+$NCH_2$); 1.86 (s, 3H, $COCH_3$); 1.14-0.98 (m, 6H, 2$CH_3$)

$^{13}$C-NMR (DMSO-$d_6$, 200 MHz): 169.97 (C=O); 168.60 (C=O); 61.43 (1C); 59.74 (2C, $OCH_2$+CH); 50.57 (1C, $NCH_2$); 47.09 and 46.84 (2C, 2$NCH_2$); 29.28 and 29.22 (2C, 2$CH_2$); 22.20 (1C, $COCH_3$); 13.83 (1C, $CH_3$); 8.85 (1C, $CH_3$);

Example 22

Synthesis of Ethyl(R,S)-(1-ethyl-4-S-nitrosomercapto-piperidin-4-yl)-[(pyridin-3-carbonyl)-amino]-acetate

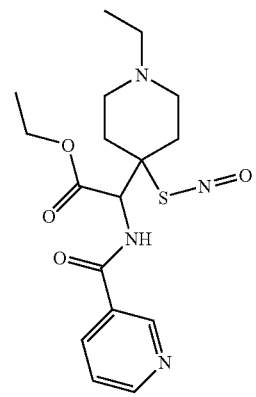

Yield last step: 76%; HPLC purity: 91.3%

By a process similar to that described in 1g, the corresponding hydrochloride is obtained: (R,S)-1-Ethyl-4-{ethoxycarbonyl-[(pyridin-3-carbonyl)-amino]-methyl}-4-S-nitrosomercapto-piperidinium chloride $^1$H-NMR (DMSO-$d_6$, 200 MHz): 11.30 (s.b., HCl); 9.39 (d., J=9 Hz, NH); 8.98 (s, 1H, H2pyridine); 8.73 (d, J=6 Hz, 1H, H6pyridine); 8.24 (d, J=7.2 Hz, 11H, H4pyridine); 7.53 (dd, J=6 Hz, $J_2$=7.2 Hz, 1H, H5pyridine); 5.52 (d, J=9 Hz, 1H, CH); 4.11 (q, 2H, $OCH_2$); 3.80-2.60 (m, 10H, 8H piperidine+$NCH_2$); 1.27-1.02 (m, 6H, 2$CH_3$)

$^{13}$C-NMR (DMSO-d$_6$, 200 MHz): 168.17 (C=O); 166.02 (C=O); 151.61 (1C); 148.35 (1C); 136.54 (1C); 129.42 (1C); 123.58 (1C); 61.56 (OCH$_2$); 60.31 (1C, CH); 59.78 (1C, C4piperidine); 50.58 (1C, NCH$_2$); 47.13 and 46.84 (2C, 2NCH$_2$); 29.37 and 28.98 (2C, 2CH$_2$piperidine); 13.84 (1C, CH$_3$); 8.87 (1C, CH$_3$)

Example 23

Synthesis of Ethyl(R,S)-acetylamino-(1-benzyl-4-S-nitrosomercapto-piperidin-4-yl)-acetate

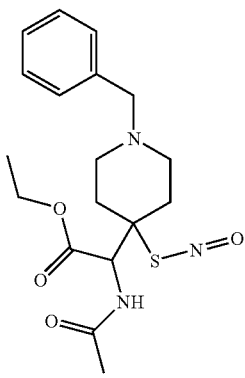

Yield last step: 86%; HPLC purity: 99.4%

$^1$H-NMR (DMSO-d$_6$, 200 MHz): 8.55 (d, J=9.2 Hz, NH); 7.30-7.23 (m, 5H, phenyl); 5.36 (d, J=9.2 Hz, 1H, CH); 4.01 (q, 2H, OCH$_2$); 3.35 (s, 2H, CH$_2$); 2.80-2.10 (m, 8H, 8Hpiperidine); 1.88 (s, 3H, COCH$_3$); 1.08 (t, 3H, CH$_3$)

$^{13}$C-NMR (DMSO-d$_6$, 200 MHz): 169.93 (C=O); 169.28 (C=O); 138.05 (1C); 128.84 (2C); 128.21 (2C); 126.94 (1C); 61.88 (1C, C4piperidine); 61.72 (OCH$_2$); 61.00 (1C, NCH$_2$Ph); 59.30 (1C, CH); 48.68 and 48.55 (2C, 2NCH$_2$); 32.43 and 31.90 (2C, 2CH$_2$); 22.22 (1C, COCH$_3$); 13.80 (1C, CH$_3$)

By a process similar to that described in 1g, the corresponding hydrochloride is obtained: (R,S)-4-(Acetylamino-ethyloxycarbonyl-methyl)-1-benzyl-4-S-nitroso-mercapto-piperidinium chloride $^1$H-NMR (DMSO-d$_6$, 200 MHz): 11.60 (s.b., HCl); 8.66 (d, J=9.2 Hz, NH); 7.63-7.37 (m, 5H, phenyl); 5.22 (d, J=9.2 Hz, 1H, CH); 4.29 (d, J=4.6 Hz, 2H, CH$_2$Ph); 4.05 (q, 2H, OCH$_2$); 3.40-2.60 (m, 8H, 8Hpiperidine); 1.85 (s, 3H, COCH$_3$); 1.08 (t, 3H, CH$_3$)

$^{13}$C-NMR (DMSO-d$_6$, 200 MHz): 169.95 (C=O); 168.58 (C=O); 131.44 (2C); 129.70 (1C); 129.38 (1C); 128.68 (2C); 61.39 (OCH$_2$); 59.82 (1C, CH); 59.72 (1C, C4piperidine); 58.55 (1C, NCH$_2$Ph); 47.37 and 47.13 (2C, 2NCH$_2$); 29.05 (2C, 2CH$_2$); 22.20 (1C, COCH$_3$); 13.78 (1C, CH$_3$)

Example 24

Synthesis of Ethyl(R,S)-(1-benzyl-4-S-nitrosomercapto-piperidin-4-yl)-[(pyridin-3-carbonyl)-amino]-acetate

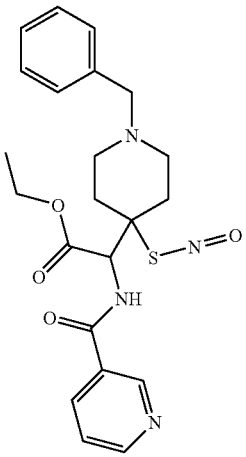

By a process similar to that described in 1g, the corresponding hydrochloride is obtained: (R,S)-1-Benzyl-4-{ethoxycarbonyl-[(pyridin-3-carbonyl)-amino]-methyl}-4-S-nitrosomercapto-piperidinium chloride $^1$H-NMR (DMSO-d$_6$, 200 MHz): 11.60 (s.b., HCl); 9.37 (d., J=9 Hz, NH); 8.97 (s, 1H, H2pyridine); 8.72 (d, J=4.4 Hz, 1H, H6pyridine); 8.24 (d, J=7.8 Hz, 1H, H4pyridine); 7.60-7.42 (m, 6H, H5pyridine+5HPh); 5.52 (d, J=9 Hz, 1H, CH); 4.31 (s.b., 2H, CH$_2$Ph); 4.09 (q, 2H, OCH$_2$); 3.80-2.80 (m, 8H, 8Hpiperidine); 1.07 (t, 3H, CH$_3$)

$^{13}$C-NMR (DMSO-d$_6$, 200 MHz): 168.16 (C=O); 166.01 (C=O); 151.54 (1C); 148.33 (1C); 136.61 (1C); 131.46 (2C); 129.71 (1C); 129.44 (2C); 128.71 (2C); 123.59 (1C); 61.55 (OCH$_2$); 60.28 (1C, CH); 59.80 (1C, C4piperidine); 58.61 (1C, NCH$_2$); 47.36 and 47.20 (2C, 2NCH$_2$); 29.27 and 28.81 (2C, 2CH$_2$piperidine); 13.82 (1C, CH$_3$).

The following products are obtained by a process similar to that described in example 17 but starting from the corresponding N-ethyl or N-benzylpiperidine compound:

Example 25

Synthesis of Ethyl(R,S)-(1-ethyl-4-S-nitrosomercapto-piperidin-4-yl)-formylamino-acetate

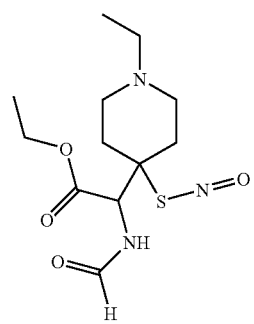

Yield last step: 82%; HPLC purity: 96.2%

$^1$H-NMR (DMSO-$d_6$, 200 MHz): 8.89 (d, J=9.4 Hz, NH); 8.08 (s, 1H, CHO); 5.36 (d, J=9.4 Hz, 1H, CH); 4.03 (q, 2H, OCH$_2$); 2.90-2.00 (m, 10H, 8H,piperidine+NCH$_2$); 1.06 (t, 3H, CH$_3$); 0.97 (t, 3H, CH$_3$)

$^{13}$C-NMR (DMSO-$d_6$, 200 MHz): 168.76 (C=O); 161.38 (C=O); 61.52 (1C, C4piperidine); 61.20 (OCH$_2$); 57.81 (1C, CH); 51.43 (1C, NCH$_2$); 48.33 and 48.2$\overline{1}$ (2C, 2NCH$_2$); 32.34 and 32.07 (2C, 2CH$_2$); 13.78 (1C, CH$_3$); 11.91 (1C, CH$_3$);

Example 26

Synthesis of Ethyl(R,S)-(1-benzyl-4-S-nitrosomercapto-piperidin-4-yl)-formylamino-acetate

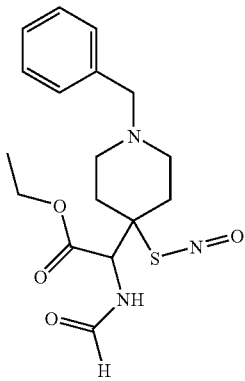

By a process similar to that described in 1g, the corresponding hydrochloride is obtained: (R,S)-1-Benzyl-4-(ethyloxycarbonyl-formylamino-methyl)-4-S-nitroso-mercapto-piperidinium chloride $^1$H-NMR (DMSO-$d_6$, 200 MHz): 11.60 (s.b., HCl); 8.98 (d, J=9.2 Hz, NH); 8.06 (s, 1H, CHO); 7.60-7.39 (m, 5H, phenyl); 5.22 (d, J=9.2 Hz, 1H, CH); 4.29 (d, J=4.4 Hz, 2H, CH$_2$Ph); 4.07 (q, 2H, OCH$_2$); 3.40-2.60 (m, 8H, 8Hpiperidine); 1.09 (t, 3H, CH$_3$)

$^{13}$C-NMR (DMSO-$d_6$, 200 MHz): 169.95 (C=O); 168.58 (C=O); 131.44 (2C); 129.70 (1C); 129.38 (1C); 128.68 (2C); 61.39 (OCH$_2$); 59.82 (1C, CH); 59.72 (1C, C4piperidine); 58.55 (1C, NCH$_2$Ph); 47.37 and 47.13 (2C, 2NCH$_2$); 29.05 (2C, 2CH$_2$); 22.20 (1C, COCH$_3$); 13.78 (1C, CH$_3$)

The following products are obtained by following a process similar to that described in example 1 but substituting ethyl isocyanoacetate with methyl isocyanoacetate in step a):

Example 27

Synthesis of Methyl(R,S)-acetylamino-(1-methyl-4-S-nitrosomercapto-piperidin-4-yl)-acetate

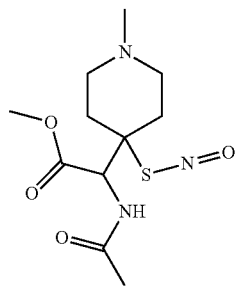

Yield last step: 50%; HPLC purity: 90.2%

$^1$H-NMR (DMSO-$d_6$, 200 MHz): 8.59 (d, J=9.2 Hz, NH); 5.37 (d, J=9.2 Hz, 1H, CH); 3.57 (s, 3H, OCH$_3$); 2.80-2.00 (m, 8H,piperidine); 2.17 (s, 3H, NCH$_3$); 1.88 (s, 3H, COCH$_3$);

$^{13}$C-NMR (DMSO-$d_6$, 200 MHz): 169.80 (2C, 2C=O); 61.14 (1C, C4piperidine); 59.33 (1C, CH); 52.02 (OCH$_3$); 50.74 and 50.61 (2C, 2NCH$_2$); 45.62 (NCH$_3$); 32.1$\overline{3}$ and 31.84 (2C, 2CH$_2$); 22.14 (1C, COCH$_3$)

By a process similar to that described in 1g, the corresponding hydrochloride is obtained: (R,S)-4-(Acetylaminomethyloxycarbonyl-methyl)-1-methyl-4-S-nitroso-mercapto-piperidinium chloride $^1$H-NMR (DMSO-$d_6$, 200 MHz): 11.48 (s.b., HCl); 8.71 (d, J=9.2 Hz, NH); 5.25 (d, J=9.2 Hz, 1H, CH); 3.62 (s, 3H, OCH$_3$); 3.60-2.70 (m, 11H, 8Hpiperidine+NCH$_3$); 1.86 (s, 3H, COCH$_3$);

$^{13}$C-NMR (DMSO-$d_6$, 200 MHz): 169.96 (1C, C=O); 169.08 (1C, C=O); 59.76 (1C, CH); 59.20 (1C, C4piperidine); 52.42 (OCH$_3$); 49.15 and 48.99 (2C, 2NCH$_2$); 41.95 (NCH$_3$); 29.42 and 29.22 (2C, 2CH$_2$); 22.18 (1C, COCH$_3$)

Example 28

Synthesis of Methyl(R,S)-(1-methyl-4-S-nitrosomercapto-piperidin-4-yl)-[(pyridin-3-carbonyl)-amino]-acetate

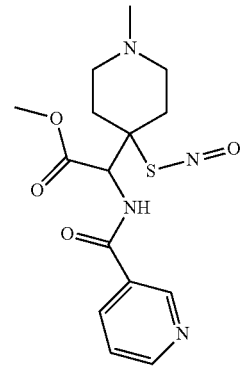

$^1$H-NMR (DMSO-$d_6$, 200 MHz): 9.20 (d., J=9 Hz, NH); 8.91 (s, 1H, H2pyridine); 8.71 (d, J=6.2 Hz, 1H, H6pyridine); 8.13 (m, 1H, H4pyridine); 7.48 (m, 1H, H5pyridine); 5.64 (d, J=9 Hz, 1H, CH); 3.63 (s, 3H, OCH$_3$); 2.80-2.10 (m, 8H, 8Hpiperidine); 2.17 (s, 3H, NCH$_3$)

$^{13}$C-NMR (DMSO-$d_6$, 200 MHz): 168.29 (C=O); 164.04 (C=O); 152.21 (1C); 148.82 (1C); 135.62 (1C); 128.16 (1C); 123.27 (1C); 61.38 (1C, C4piperidine); 60.24 (1C, CH); 52.29 (OCH$_3$); 50.80 and 50.63 (2C, 2NCH$_2$); 45.63 (1C, NCH$_3$); 3$\overline{2}$.22 and 32.04 (2C, 2CH$_2$piperidine)

Example 29

Methyl(R,S)-benzenesulfonylamino-(1-methyl-4-S-nitrosomercapto-piperidin-4-yl)-acetate

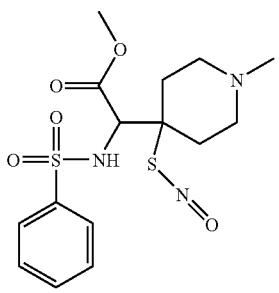

Yield last step: 50%; HPLC purity: 95.6%

$^1$H-NMR (CDCl$_3$, 200 MHz): 7.82-7.44 (m, 5H); 4.53 (s, 1H, CH); 3.25 (s, 3H, OCH$_3$); 2.80-2.20 (m, 8H, piperidine); 2.29 (s, NCH$_3$)

$^{13}$C-NMR (CDCl$_3$, 200 MHz): 169.02 (C=O); 139.17 (1C); 132.98 (1C); 129.03 (2C); 127.38 (2C); 64.18 (1C, CH); 60.12 (1C, C4piperidine); 52.30 (1C, OCH$_3$); 51.02 and 50.91 (2C, 2NCH$_2$); 45.85 (NCH$_3$); 33.61 and 33.10 (2C, 2CH$_2$piperidine)

By a process similar to that described in 1g, the corresponding hydrochloride is obtained: (R,S)-4-(Benzenesulfonylamino-methoxycarbonyl-methyl)-1-methyl-4-S-nitrosomercapto-piperidinium chloride $^1$H-NMR (DMSO-d$_6$, 200 MHz): 11.47 (s.b., 1H, HCl); 8.86 (d, J=10.4 Hz, 1H, NH); 7.83-7.51 (m, 5H); 4.51 (d, J=10.4 Hz, 1H, CH); 3.22 (s, 3H, OCH$_3$); 3.60-2.70 (m, 1H, 8H piperidine+NCH$_3$)

$^{13}$C-NMR (DMSO-d$_6$, 200 MHz): 167.98 (C=O); 139.97 (1C); 132.76 (1C); 129.02 (2C); 126.59 (2C); 64.22 (1C, CH); 58.84 (1C, C4piperidine); 52.18 (1C, OCH$_3$); 49.08 and 48.85 (2C, 2NCH$_2$); 41.98 (NCH$_3$); 29.69 and 28.60 (2C, 2CH$_2$piperidine)

The following product is obtained by a process similar to that described in example 17 but starting from the corresponding compound with methyl ester instead of ethyl ester:

Example 30

Synthesis of Methyl(R,S)-formylamino-(1-methyl-4-S-nitrosomercapto-piperidin-4-yl)-acetate

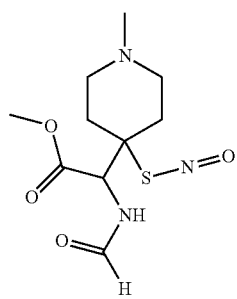

$^1$H-NMR (DMSO-d$_6$, 200 MHz): 8.91 (d, J=9.6 Hz, NH); 8.08 (s, 1H, CHO); 5.38 (d, J=9.6 Hz, 1H, CH); 3.60 (s, 3H, OCH$_3$); 2.90-2.10 (m, 11H, 8Hpiperidine+NCH$_3$)

$^{13}$C-NMR (DMSO-d$_6$, 200 MHz): 168.47 (C=O); 161.19 (C=O); 60.88 (1C, C4piperidine); 57.85 (1C, CH); 54.88 (1C, OCH$_3$); 50.66 and 50.55 (2C, 2NCH$_2$); 45.48 (NCH$_3$); 32.13 (2C, 2CH$_2$piperidine)

Example 31

Synthesis of Ethyl(R,S)-acetylamino-(4-nitrosomercapto-tetrahydro-thiopyran-4-yl)-acetate

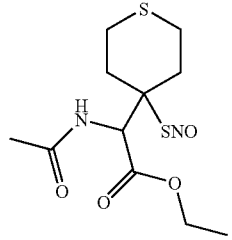

The product of the example is obtained by following a process similar to that described in examples 1a-1f and starting from the 4-tetrahydrothiopyranone.

$^1$H-NMR (CDCl$_3$, 200 MHz): 6.44 (d, NH); 5.42 (d, J=9.6 Hz, 1H, CH); 4.10 (q, 2H, OCH$_2$); 3.20-2.40 (m, 8H, thiopyran); 2.13 (s, 3H, COCH$_3$); 1.17 (t, 3H, CH$_3$)

$^{13}$C-NMR (CDCl$_3$, 200 MHz): 170.13 (C=O); 169.32 (C=O); 62.36 (1C, C4thiopyran); 61.81 (1C, OCH$_2$); 59.58 (1C, CH); 34.78 and 34.38 (2C, 2CH$_2$); 23.62 and 23.56 (2C, 2CH$_2$); 22.99 (1C, COCH$_3$); 13.77 (1C, CH$_3$)

Example 32

Synthesis of Ethyl(R,S)-benzenesulfonylamino-(4-nitrosomercapto-tetrahydro-thiopyran-4-yl)-acetate

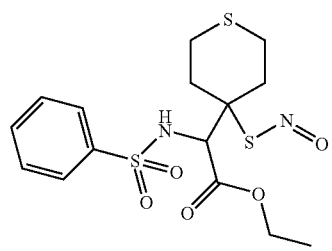

$^{13}$C-NMR (CDCl$_3$, 200 MHz): 168.30 (C=O); 139.07 (1C); 132.90 (1C); 128.86 (2C); 127.07 (2C); 63.93 (1C, CH); 61.79 (1C, C4thiopyran); 61.50 (1C, OCH$_2$); 34.22 (2C, 2CH$_2$); 23.39 (2C, 2CH$_2$); 13.39 (1C, CH$_3$)

Example 33

Stability Study

The stability of the S-nitrothiol compounds of the invention was determined by placing the compounds at 5° C. and 25° C. in a closed borosilicate glass vial. After 1, 2, 3, 4, and 6 months, the compounds were analysed by HPLC and detected at 201 and 345 nm.

Thus, compound of example 1g was stable for 2.5 months at 25° C. and more than 10 months at 4° C.; compound of example 7 as hydrochloride salt was stable at least 4 months at 25° C. and more then 6 months at 4° C.

Therefore, it is clear that the compounds of the invention present a much better stability than the prior art S-nitrothiol compounds like GSNO (stable 1 day at 25° C.), or N-acetyl-2-amino-2[4-(4-S-nitrosomercapto-1-methylpiperidin)]acetic acid [example 2 of EP 1157987] (stable 2 days at 25° C.).

Note: it has been considered that a compound is no longer stable when it looses more than 5% of its initial purity value.

B) Pharmacology

The activity of the products was assessed in experimental animals in accordance with the European Community Standards on the Care and Use of Laboratory Animals and approved by the Animal Care and Use Committee of local authorities. Two experimental models to test antithrombotic activity in rats were used: Arterio-Venous Shunt and Ferric chloride arterial thrombosis model. Additionally, the effect of the products on the systemic blood pressure was investigated.

Example 36

Rat Arterial Thrombosis Model

Fasted male Wistar rats (300-320 g; Janvier, Le Genest St. Isle, France) were anesthetized with sodium pentobarbital (60 mg/kg i.p.) and thermoregulated by use of blankets (Biosis homeothermic blanket control unit; Biosis, Spain). A segment (approximately 1-cm long) of the left carotid artery was exposed and fitted at the distal end with an appropriately sized Doppler flow probe. Thrombosis was induced by applying a 70% ferric chloride solution embedded patch onto the artery. Blood flow velocity was measured using a Doppler flowmeter (Transonic Systems, San Diego, Calif.) and data recorded using a system for acquisition of data (Acqk). Blood flow was recorded for 60 min post-lesion. When the flow declined to zero, the time in minutes to thrombus formation was noted. The protocol followed was originally described by Feuerstein G Z, et al Artherioscler. Thromb. Vasc. Biol. 1999, 19: 2554-2562 and modified by Kurz K D, et al Thromb. Res. 1990, 60:269-280.

The number of animals presenting no occlusion 30 min post-lesion were also noted. Products were dissolved in saline and were given as an i.v. infusion for 30 minutes. $ED_{50}$ for each product was calculated and results are shown in Table 1

TABLE 1

| Compound | $ED_{50}$ (μg/kg, i.v.) |
| --- | --- |
| GSNO | 18.1 |
| N-acetyl-2-amino-2[4-(4-S-nitroso-mercapto-1-methylpiperidin)]acetic acid [example 2 of EP 1157987] | 4.1 |
| Example 1g | 9.1 |
| Example 7 (hydrochloride salt) | 56.4 |

Anti-thrombotic effect of compounds compared with reference compound in rat arterial thrombosis model after i.v. administration for 30 minutes. Values shown are the mean values with 95% confidence limits.

Example 37

Rat Arterio-Venous Shunt-Silk Thread Model

Fasted male Wistar rats (300-320 g; Janvier, Le Genest St. Isle, France) were anesthetized with sodium pentobarbitone (60 mg/kg i.p.). An arterio-venous (AV) shunt was prepared according to the technique of Umetsu and Sanai (1978). Two 12 cm-long polyethylene tubes (0.85- and 1.27-mm i.d. and o.d., respectively) linked to a central part (6 cm-long; 1.14-mm i.d.) containing a 5-cm cotton thread and filled with heparised (25 u/ml) saline solution were placed between the right carotid artery and the left jugular vein. All products were given i.v through the jugular vein for 60 minutes. Shunt was placed 45 minutes after the initiation of the perfusion with the testing substances and removed at the end of the perfusion i.e. after 15 min of blood circulation. Cotton thread supporting the thrombus was extracted. The wet weight of the thrombus was determined and the % of anti-thrombotic protection was calculated and shown in Table 2.

TABLE 2

| Compound | Dose (μg/kg, i.v.) | Antithrombotic protection (%) |
| --- | --- | --- |
| GSNO | 4.0 | 58 |
| N-acetyl-2-amino-2[4-(4-S-nitrosomercapto-1-methyl-piperidin)]acetic acid [example 2 of EP 1157987] | 1.7 | 61 |
| Example 1g | 2.0 | 54 |
| Example 7 (hydrochloride salt) | 10.4 | 60 |

Anti-thrombotic effect of compounds compared with reference compound in rat arterio-venous shunt model after i.v. administration.

Example 38

Effect of Nitrosothiols on Systemic Blood Pressure

Fasted male Wistar rats (300-320 g; Janvier, Le Genest St. Isle, France) were anesthetized with sodium pentobarbitone (60 mg/kg i.p.). The effect of treatments on systemic blood pressure was tested. Products dissolved in saline solution and were infused intravenously for 30 minutes at 0.5 ml/h. Dose of product given was 100 times the antithrombotic ED50 determined in the arterial thrombosis model. Basal blood pressure was measured before initiation of the treatment and was recorded throughout the treatment period using a pressure transducer connected to the carotid artery. The change in blood pressure was expressed as a % of change vs. basal values.

TABLE 3

| Compound $DE_{50} \times 100$ (μg/kg, i.v.) | Mean arterial pressure (mm Hg) | | Change (%) |
| --- | --- | --- | --- |
| | Basal | After 30 min infusion | |
| GSNO | 112.2 ± 6.2 | 98.8 ± 4.1 | −12.0 |
| N-acetyl-2-amino-2[4-(4-S-nitrosomercapto-1-methyl-piperidin)]acetic acid [example 2 of EP 1157987] | 99.6 ± 2.1 | 95.1 ± 2.4 | −4.5 |
| Example 1g | 115.7 ± 8.3 | 113.6 ± 9.2 | −1.8 |
| Example7 (hydrochloride salt) | 117.9 ± 10.2 | 118.8 ± 11.1 | +0.8 |

Effect of compounds on blood pressure after i.v. administration

Example 38

Effect of Nitrosothiols on Alfa-chymotrypsin-induced Glaucoma

The method used was that described by Gabriele Campana, Claudio Bucolo, Giovanna Murari and Santi Spampinato in Pharmacol. Exp Therap Vol. 303, Issue 3, 1086-1094, December 2002

Animals were injected with intra muscular injection of dexamethasone at the dose rate of 10 mg/Kg body weight, to avoid immediate inflammation. Animals were anesthetized with ketamine (50 mg/kg IV) in combination with Dizepam. Xylocalne (4%) was used for local anesthesia topically. A cannula attached to reservoir was inserted into the anterior chamber with the help of a 30 gauge needle to provide a hydrostatic pressure of 25 mmHg during injection of alpha-chymotrypsin. Then a second appropriately shaped 30 gauge needle was introduced near the pupil. Freshly prepared 150 units of alpha chymotrypsin prepared in 0.1 ml of sterile saline was irrigated through the cannula into the posterior chamber. Care was taken to prevent the contact of alpha chymotrypsin with corneal stroma. Both cannulas were carefully removed without significant loss of aqueous humor. Immediately after surgery the eye treated with Sofracort (Corticosteroid) to reduce the chances of fungal or microbial infection.

All the animals were kept under observation for 5 days and after these five days the intraocular pressure (IOP) was measured daily with a Schiontz type indentation tonometer using 5.5 gm weights and by compilation of readings the maximum period required to achieve a stable increase in IOP was determined. It was found that 2-3 weeks were sufficient to achieve a stable increase in IOP. IOP was measured after 15 days for 3 consecutive days, every morning (at same time) to assure stable IOP. The rejection criteria in our study was the removal of those rabbits from the study which showed IOP<30 mmHg.

Treatment:

All the animals were closely observed for the development of glaucoma. Thirty animals showing the symptoms of glaucoma and with the intra ocular pressure more than 30 mmHg were selected for the present investigation.

Compound (R,S)-4-(Acetylamino-ethoxycarbonyl-methyl)-1-methyl-4-S-nitroso-mercapto-piperidinium chloride (example 1g) was administered to a group of rabbits at a concentration of 0.05% by weight [0.05 g in 100 mL of saline serum] by 3 drops instillation. For comparative data, the compound Timolol (Timoftol®) widely used for the treatment of glaucoma, was also administered to another group of rabbits at a concentration of 0.5% by weight.

The intraocular pressure measurements are included in the table 2 in mm Hg taken at 0, 1 and 2 h after 3 drops instillation.

| Group | Treatment | 0 hr | 1 hr | 2 hr |
|---|---|---|---|---|
| Gr I | Example 1g | 34.33 ± 0.68 | 24.72 ± 0.47 | 23.86 ± 0.32 |
| Gr II | Timolol 0.5% (Timoftol ® 0.5%) | 34.45 ± 0.58 | 24.77 ± 0.26 | 24.54 ± 0.26 |
| control | Normal saline | 33.76 ± 0.54 | 33.21 ± 0.34 | 32.37 ± 0.31 |

These results point out that compound of example 1g of the present invention significantly reduces the intraocular pressure showing similar results to those obtained with a conventional compound even when using 10-fold lower concentrations.

The invention claimed is:

1. A compound of formula (I)

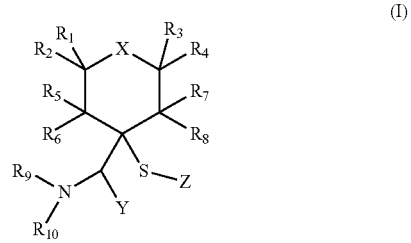

wherein
$R_1$ and $R_3$ are each independently selected from the group consisting of hydrogen, alkyl, alkenyl, cycloalkyl and alkynyl;
$R_2$, $R_4$, $R_5$, $R_6$, $R_7$ and $R_8$ are each independently selected from the group consisting of hydrogen, alkyl, alkenyl, cycloalkyl and alkynyl;
$R_9$ is selected from the group consisting of hydrogen, alkyl, alkenyl, cycloalkyl, alkynyl, aryl and aralkyl;
$R_{10}$ is selected from the group consisting of hydrogen, alkyl, cycloalkyl, alkenyl, alkynyl, heterocyclyl, —C(=O)$R_{11}$ and —S(=O)$_2R_{11}$, wherein $R_{11}$ is selected from the group consisting of hydrogen, alkyl, alkenyl, cycloalkyl, alkynyl, aryl, aralkyl and heterocyclyl;
Z is NO;
Y is an alkoxycarbonyl of formula —C(=O)O$R_{12}$, wherein $R_{12}$ is selected from the group consisting of alkyl, alkenyl, cycloalkyl, alkynyl, aryl, aralkyl, and heterocyclyl; and
X is —N$R_{13}$; wherein $R_{13}$ is selected from the group consisting of hydrogen, alkyl, alkenyl, cycloalkyl, alkynyl, aryl, aralkyl and heterocyclyl;
or its salts thereof.

2. Compound according to claim 1 wherein each of $R_5$, $R_6$, $R_7$ and $R_8$ is hydrogen.

3. Compound according to claim 1 of formula (II):

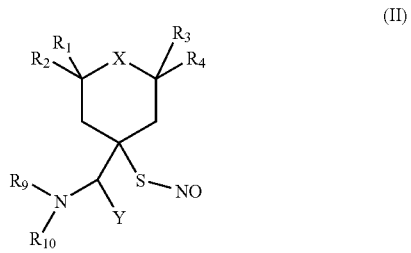

wherein
$R_1$ and $R_3$ are each independently selected from the group consisting of hydrogen and $C_1$-$C_4$ alkyl;
$R_2$ and $R_4$ are each independently selected from the group consisting of hydrogen and $C_1$-$C_4$ alkyl;
$R_9$ is selected from the group consisting of hydrogen, $C_1$-$C_6$ alkyl and $C_7$-$C_{15}$ aralkyl;
$R_{10}$ is selected from the group consisting of hydrogen, $C_1$-$C_6$ alkyl, $C_3$-$C_8$ cycloalkyl, —C(=O)$R_{11}$ and —S(=O)$_2$R$_{11}$, wherein R$_{11}$ is selected from the group consisting of hydrogen, C$_1$-C6 alkyl, C$_2$-C$_6$ alkenyl, C$_3$-C$_8$ cycloalkyl, C$_2$-C$_6$ alkynyl, C$_6$-C$_{10}$ aryl, C$_7$-C$_{10}$ aralkyl and heterocyclyl;

Y is an alkoxycarbonyl of formula —C(=O)OR$_{12}$, wherein R$_{12}$ is selected from the group consisting of C$_1$-C$_6$ alkyl, C$_2$-C$_6$ alkenyl, C$_3$-C$_8$ cycloalkyl, C$_2$-C$_6$ alkynyl, C$_6$—$_{C10}$ aryl, C$_7$-C$_{10}$ aralkyl and heterocyclyl; and X is NR$_{13}$, wherein R$_{13}$ is selected from the group consisting of hydrogen, C$_1$-C$_6$ alkyl group, C$_2$-C$_6$ alkenyl, C$_3$-C$_8$ cycloalkyl, C$_2$-C$_6$ alkynyl, C$_6$-C$_{10}$ aryl, C$_7$-C$_{10}$ aralkyl and heterocyclyl;

or its salts thereof.

4. Compound according to claim 1, wherein each of R$_1$, R$_2$, R$_3$ and R$_4$ is hydrogen.

5. Compound according to claim 1, wherein R$_9$ is selected from the group consisting of hydrogen and C$_1$-C$_6$ alkyl.

6. Compound according to claim 1, wherein R$_{12}$ is a C$_1$-C$_6$ alkyl group.

7. Compound according to claim 1, wherein one of R$_9$ or R$_{10}$ is hydrogen.

8. Compound according to claim 1 of formula (IIa)

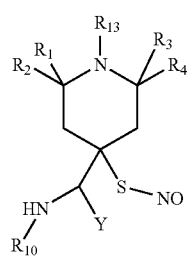

(IIa)

wherein

R$_1$ and R$_3$ are each independently selected from the group consisting of hydrogen and C$_1$-C$_4$ alkyl;

R$_2$ and R$_4$ are each independently selected from the group consisting of hydrogen and C$_1$-C$_4$ alkyl;

R$_{10}$ is selected from the group consisting of —C(=O)R$_{11}$ and —S(=O)$_2$R$_{11}$, wherein R$_{11}$ is selected from the group consisting of H, C$_1$-C$_6$ alkyl, C$_6$-C$_{10}$ aryl, C$_7$-C$_{10}$ aralkyl and heterocyclyl; and Y is an alkoxycarbonyl of formula —C(=O)OR$_{12}$, wherein R$_{12}$ is a C$_1$-C$_6$ alkyl;

or its salts thereof.

9. Compound according to claim 1 selected from the group consisting of:

Ethyl(R,S)-acetylamino-(1-methyl-4-S-nitrosomercapto-piperidin-4-yl)-acetate;

(R,S)-4-(Acetylamino-ethoxycarbonyl-methyl)-1-methyl-4-S-nitrosomercapto-piperidinium chloride;

Ethyl(R,S)-heptanoylamino-(1-methyl-4-S-nitrosomercapto-piperidin-4-yl)-acetate;

(R,S)-4-(Heptanoylamino-ethoxycarbonyl-methyl)-1-methyl-4-S-nitrosomercapto-piperidinium chloride;

Ethyl(R,S)-benzoylamino-(1-methyl-4-S-nitrosomercapto-piperidin-4-yl)-acetate;

(R,S)-4-(Benzoylamino-ethoxycarbonyl-methyl)-1-methyl-4-S-nitrosomercapto-piperidinium chloride;

Ethyl(R,S)-(4-chloro-benzoylamino)-(1-methyl-4-S-nitrosomercapto-piperidin-4-yl)-acetate;

(R,S)-4-[(4-Chloro-benzoylamino)-ethoxycarbonyl-methyl)]-1-methyl-4-S-nitrosomercapto-piperidinium chloride;

Ethyl(R,S)-(2-chloro-benzoylamino)-(1-methyl-4-S-nitrosomercapto-piperidin-4-yl)-acetate;

(R,S)-4-[(2-Chloro-benzoylamino)-ethoxycarbonyl-methyl)]-1-methyl-4-S-nitrosomercapto-piperidinium chloride;

Ethyl(R,S)-(1-methyl-4-S-nitrosomercapto-piperidin-4-yl)-[(pyridin-3-carbonyl)-amino]-acetate;

(R,S)-4-{Ethoxycarbonyl-[(pyridin-3-carbonyl)-amino]-methyl}-1-methyl-4-S-nitrosomercapto-piperidinium chloride;

Ethyl(R,S)-benzenesulfonylamino-(1-methyl-4-S-nitrosomercapto-piperidin-4-yl)-acetate;

(R,S)-4-(Benzenesulfonylamino-ethoxycarbonyl-methyl)-1-methyl-4-S-nitrosomercapto-piperidinium chloride;

Ethyl(R,S)-(1-methyl-4-S-nitrosomercapto-piperidin-4-yl)-(4-nitro-benzene sulfonylamino)-acetate;

Ethyl(R,S)-(4-methyl-benzenesulfonylamino)-(1-methyl-4-S-nitrosomercapto-piperidin-4-yl)-acetate;

Ethyl(R,S)-(2-chloro-benzenesulfonylamino)-(1-methyl-4-S-nitrosomercapto-piperidin-4-yl)-acetate;

Ethyl(R,S)-(3-chloro-benzenesulfonylamino)-(1-methyl-4-S-nitrosomercapto-piperidin-4-yl)-acetate;

Ethyl(R,S)-(4-chloro-benzenesulfonylamino)-(1-methyl-4-S-nitrosomercapto-piperidin-4-yl)-acetate;

(R,S)-4-(4-Chloro-benzenesulfonylamino-ethoxycarbonyl-methyl)-1-methyl-4-S-nitrosomercapto-piperidinium chloride;

(R,S)-4-(2-Fluoro-benzenesulfonylamino-ethoxycarbonyl-methyl)-1-methyl-4-S-nitrosomercapto-piperidinium chloride;

Ethyl(R,S)-(4-fluoro-benzenesulfonylamino)-(1-methyl-4-S-nitrosomercapto-piperidin-4-yl)-acetate;

(R,S)-4-(4-Fluoro-benzenesulfonylamino-ethoxycarbonyl-methyl)-1-methyl-4-S-nitrosomercapto-piperidinium chloride;

Ethyl(R,S)-(2,4-difluoro-benzenesulfonylamino)-(1-methyl-4-S-nitroso mercapto-piperidin-4-yl)-acetate;

(R,S)-4-(2,4-Difluoro-benzenesulfonylamino-ethoxycarbonyl-methyl)-1-methyl-4-S-nitrosomercapto-piperidinium chloride;

Ethyl(R,S)-formylamino-(1-methyl-4-S-nitrosomercapto-piperidin-4-yl)-acetate;

(R,S)-4-(Ethoxycarbonyl-formylamino-methyl)-1-methyl-4-S-nitrosomercapto-piperidinium chloride;

Ethyl(R,S)-(1-methyl-4-S-nitrosomercapto-piperidin-4-yl)-(2,2,2-trifluoro-acetylamino)-acetate;

Benzyl(R,S)-acetylamino-(1-methyl-4-S-nitrosomercapto-piperidin-4-yl)-acetate;

Ethyl(R,S)-(acetyl-ethyl-amino)-(1-methyl-4-S-nitrosomercapto-piperidin-4-yl)-acetate;

Ethyl(R,S)-acetylamino-(1-ethyl-4-S-nitrosomercapto-piperidin-4-yl)-acetate;

(R,S)-4-(Acetylamino-ethyloxycarbonyl-methyl)-1-ethyl-4-S-nitrosomercapto-piperidinium chloride;

Ethyl(R,S)-(1-ethyl-4-S-nitrosomercapto-piperidin-4-yl)-[(pyridin-3-carbonyl)-amino]-acetate;

(R,S)-1-Ethyl-4-{ethoxycarbonyl-[(pyridin-3-carbonyl)-amino]-methyl}-4-S-nitrosomercapto-piperidinium chloride;

Ethyl(R,S)-acetylamino-(1-benzyl-4-S-nitrosomercapto-piperidin-4-yl)-acetate;

(R,S)-4-(Acetylamino-ethyloxycarbonyl-methyl)-1-benzyl-4-S-nitrosomercapto-piperidinium chloride;

Ethyl(R,S)-(1-benzyl-4-S-nitrosomercapto-piperidin-4-yl)-[(pyridin-3-carbonyl)-amino]-acetate;

(R,S)-1-Benzyl-4-{ethoxycarbonyl-[(pyridin-3-carbonyl)-amino]-methyl}-4-S-nitrosomercapto-piperidinium chloride;
Ethyl(R,S)-(1-ethyl-4-S-nitrosomercapto-piperidin-4-yl)-formylamino-acetate;
(R,S)-1-Ethyl-4-(ethyloxycarbonyl-formylamino-methyl)-4-S-nitrosomercapto-piperidinium chloride;
Ethyl(R,S)-(1-benzyl-4-S-nitrosomercapto-piperidin-4-yl)-formylamino-acetate;
(R,S)-1-Benzyl-4-(ethyloxycarbonyl-formylamino-methyl)-4-S-nitrosomercapto-piperidinium chloride;
Methyl(R,S)-acetylamino-(1-methyl-4-S-nitrosomercapto-piperidin-4-yl)-acetate;
(R,S)-4-(Acetylamino-methyloxycarbonyl-methyl)-1-methyl-4-S-nitrosomercapto-piperidinium chloride;
Methyl(R,S)-(1-methyl-4-S-nitrosomercapto-piperidin-4-yl)-[(pyridin-3-carbonyl)-amino]-acetate;
Methyl(R,S)-benzenesulfonylamino-(1-methyl-4-S-nitrosomercapto-piperidin-4-yl)-acetate;
(R,S)-4-(Benzenesulfonylamino-methoxycarbonyl-methyl)-1-methyl-4-S-nitrosomercapto-piperidinium chloride; and
Methyl(R,S)-formylamino-(1-methyl-4-S-nitrosomercapto-piperidin-4-yl)-acetate;
or salts thereof.

10. Pharmaceutical composition comprising a compound as defined in claim 1 and a pharmaceutically acceptable carrier.

11. A method for the treatment and/or inhibition of a condition selected from the group consisting of platelet aggregation dysfunction, vascular musculature dysfunction and, occular hypertension said method comprising administering to a patient in need of such treatment a therapeutically effective amount of a compound according to claim 1.

12. Method according to claim 11 wherein said condition is selected from the group consisting of hypertension, thrombosis, thromboembolic processes, ischemia-reperfusion, carotid endarterectomy and coronary bypass, in percutaneous coronary interventions, pulmonary hypertension, portal hypertension, erectile dysfunction, and glaucoma.

13. Method for the synthesis of a compound of formula (I) as defined in claim 1 comprising the following steps:
a) the addition of a compound of formula HS—Z, wherein Z is selected from the group consisting of unsubstituted alkyl, alkenyl, $C_7$-$C_{20}$ aralkyl, —Si(R')$_3$ and —C(=O)R' wherein R' is selected from the group consisting of alkyl, alkenyl, cycloalkyl, alkynyl, aryl and aralkyl; in the presence of a base, to a compound of formula (V)

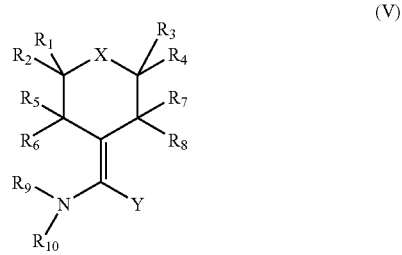

(V)

wherein
$R_1$ and $R_3$ are each independently selected from the group consisting of hydrogen, alkyl, alkenyl, cycloalkyl and alkynyl; $R_2$, $R_4$, $R_5$, $R_6$, $R_7$ and $R_8$ are each independently selected from the group consisting of hydrogen, alkyl, alkenyl, cycloalkyl and alkynyl;

$R_9$ is selected from the group consisting of hydrogen, alkyl, alkenyl, cycloalkyl, alkynyl, aryl and aralkyl;

$R_{10}$ is selected from the group consisting of hydrogen, alkyl, cycloalkyl, alkenyl, alkynyl, heterocyclyl, —C(=O)$R_{11}$ and —S(=O)$_2 R_{11}$, wherein $R_{11}$ is selected from the group consisting of hydrogen, alkyl, alkenyl, cycloalkyl, alkynyl, aryl, aralkyl and heterocyclyl;

Y is an alkoxycarbonyl of formula —C(=O)O$R_{12}$, wherein $R_{12}$ is selected from the group consisting of alkyl, alkenyl, cycloalkyl, alkynyl, aryl, aralkyl, and heterocyclyl; and X is —N$R_{13}$; wherein $R_{13}$ is selected from the group consisting of hydrogen, alkyl, alkenyl, cycloalkyl, alkynyl, aryl, aralkyl and heterocyclyl;

or its salts thereof b) the removal of the Z group from a compound of formula (IV) obtained in step a)

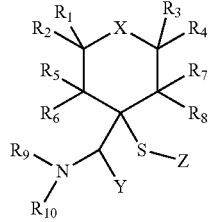

(IV)

wherein
$R_1$ and $R_3$ are each independently selected from the group consisting of hydrogen, alkyl, alkenyl, cycloalkyl and alkynyl;

$R_2$, $R_4$, $R_5$, $R_6$, $R_7$ and $R_8$ are each independently selected from the group consisting of hydrogen, alkyl, alkenyl, cycloalkyl and alkynyl;

$R_9$ is selected from the group consisting of hydrogen, alkyl, alkenyl, cycloalkyl, alkynyl, aryl and aralkyl;

$R_{10}$ is selected from the group consisting of hydrogen, alkyl, cycloalkyl, alkenyl, alkynyl, heterocyclyl, —C(=O)$R_{11}$ and —S(=O)$_2 R_{11}$, wherein $R_{11}$ is selected from the group consisting of hydrogen, alkyl, alkenyl, cycloalkyl, alkynyl, aryl, aralkyl and heterocyclyl;

Z is selected from the group consisting of unsubstituted alkyl, alkenyl, $C_7$-$C_{20}$ aralkyl, —Si(R')$_3$ and —C(=O)R', wherein R' is selected from the group consisting of alkyl, alkenyl, alkynyl, aryl and aralkyl;

Y is an alkoxycarbonyl of formula —C(=O)O$R_{12}$, wherein $R_{12}$ is selected from the group consisting of alkyl, alkenyl, cycloalkyl, alkynyl, aryl, aralkyl, and heterocyclyl; and X is —N$R_{13}$; wherein $R_{13}$ is selected from the group consisting of hydrogen, alkyl, alkenyl, cycloalkyl, alkynyl, aryl, aralkyl and heterocyclyl;

or its salts thereof; and c) the nitrosation of the thiol functionality of the compound obtained in step b) for obtaining a compound of formula (I).

14. Method according to claim 13, wherein said nitrosation comprises contacting a compound obtained in step (b) with a reagent selected from the group consisting of nitrous acid, alkylnitrites, NO gas, NOCl, NOBr, $N_2O_3$, $N_2O_4$, and BrCH$_2$NO$_2$.

15. Method according to claim 14, wherein said reagent is produced in situ in the reaction media.

16. Method for the synthesis of a compound of formula (I) as defined in claim 1 comprising the following steps:
   a) the addition of $SH_2$ in the presence of a base, to a compound of formula (V)

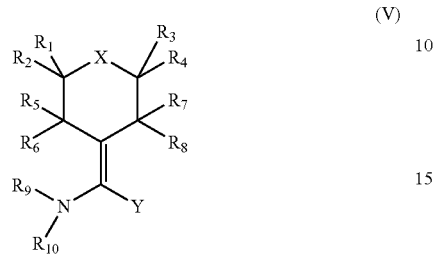

(V)

wherein
   $R_1$ and $R_3$ are each independently selected from the group consisting of hydrogen, alkyl, alkenyl, cycloalkyl and alkynyl; $R_2$, $R_4$, $R_5$, $R_6$, $R_7$ and $R_8$ are each independently selected from the group consisting of hydrogen, alkyl, alkenyl, cycloalkyl and alkynyl;
   $R_9$ is selected from the group consisting of hydrogen, alkyl, alkenyl, cycloalkyl, alkynyl, aryl and aralkyl;
   $R_{10}$ is selected from the group consisting of hydrogen, alkyl, cycloalkyl, alkenyl, alkynyl, heterocyclyl, —C(=O)$R_{11}$ and —S(=O)$_2R_{11}$, wherein $R_{11}$ is selected from the group consisting of hydrogen, alkyl, alkenyl, cycloalkyl, aryl, aralkyl and heterocyclyl;
   Y is an alkoxycarbonyl of formula —C(=O)0$R_{12}$, wherein $R_{12}$ is selected from the group consisting of alkyl, alkenyl, cycloalkyl, alkynyl, aryl, aralkyl, and heterocyclyl; and
   X is —N$R_{13}$; wherein $R_{13}$ is selected from the group consisting of hydrogen, alkyl, alkenyl, cycloalkyl, alkynyl, aryl, aralkyl and heterocyclyl;
   or its salts thereof and
   b) the nitrosation of the thiol functionality of the compound obtained in step a) for obtaining a compound of formula (I).

17. Method according to claim 16, wherein said nitrosation comprises contacting the compound obtained in step a) with a reagent selected from the group consisting of nitrous acid, alkylnitrites, NO gas, NOCl, NOBr, $N_2O_3$, $N_2O_4$, and BrCH$_2$NO$_2$.

* * * * *

UNITED STATES PATENT AND TRADEMARK OFFICE
CERTIFICATE OF CORRECTION

PATENT NO. : 8,012,993 B2
APPLICATION NO. : 11/680815
DATED : September 6, 2011
INVENTOR(S) : Moliner et al.

It is certified that error appears in the above-identified patent and that said Letters Patent is hereby corrected as shown below:

Column 49, line 8: change "$C_{6-C10}$" to -- $C_6$-$C_{10}$ --

Signed and Sealed this
Twenty-ninth Day of November, 2011

David J. Kappos
*Director of the United States Patent and Trademark Office*